US 11,169,089 B2

(12) United States Patent
Noda et al.

(10) Patent No.: US 11,169,089 B2
(45) Date of Patent: Nov. 9, 2021

(54) SURFACE PLASMON RESONANCE MEASUREMENT METHOD FOR MEASURING AMOUNT OF SUBSTANCE IN A SPECIMEN INCLUDING WHOLE BLOOD

(71) Applicant: Konica Minolta, Inc., Tokyo (JP)

(72) Inventors: Tetsuya Noda, Hino (JP); Fumio Nagai, Hachioji (JP); Youichi Aoki, Toda (JP); Makiko Otani, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 460 days.

(21) Appl. No.: 16/328,437

(22) PCT Filed: Sep. 6, 2017

(86) PCT No.: PCT/JP2017/032132
§ 371 (c)(1),
(2) Date: Feb. 26, 2019

(87) PCT Pub. No.: WO2018/051863
PCT Pub. Date: Mar. 22, 2018

(65) Prior Publication Data
US 2021/0285874 A1 Sep. 16, 2021

(30) Foreign Application Priority Data

Sep. 14, 2016 (JP) .............................. JP2016-179396

(51) Int. Cl.
*G01N 21/552* (2014.01)
*G01N 21/49* (2006.01)
(Continued)

(52) U.S. Cl.
CPC ........... *G01N 21/553* (2013.01); *G01N 21/49* (2013.01); *G01N 21/648* (2013.01); *G01N 33/49* (2013.01); *G01N 33/54373* (2013.01)

(58) Field of Classification Search
CPC .... G01N 21/553; G01N 21/552; G01N 21/64; G01N 21/648; G01N 33/543; G01N 33/54373; G01N 21/49; G01N 33/49
(Continued)

(56) References Cited

U.S. PATENT DOCUMENTS 9,435,919 B2 * 9/2016 Umetsu .................... G02B 5/04
10,061,064 B2 * 8/2018 Umetsu .................... G02B 5/04
(Continued)

FOREIGN PATENT DOCUMENTS

WO 2015/129615 A1 9/2015
WO 2016/039149 A1 3/2016

OTHER PUBLICATIONS

International Search Report dated Nov. 28, 2017 from the corresponding International Application No. PCT/JP2017/032132 and English translation.

*Primary Examiner* — Roy M Punnoose
(74) *Attorney, Agent, or Firm* — Lucas & Mercanti, LLP

(57) ABSTRACT

A measurement chip including a prism, a metal film, and a capturing body is prepared. In a state in which a specimen is present on the metal film, scattered light obtained when first light which passes through the metal film and the specimen is scattered in the specimen when the first light is applied to the metal film from a prism side at a first incident angle smaller than a critical angle is detected. In a state in which a substance to be measured is captured by the capturing body and the specimen is not present on the metal film, a signal indicating an amount of the substance to be measured generated in the measurement chip when second light is applied to the metal film at a second incident angle not smaller than the critical angle from the prism side is detected. On the basis of a hematocrit value of the specimen determined from a light amount of the scattered light, a (Continued)

measurement value indicating the amount of the substance to be measured determined from the signal is corrected.

20 Claims, 9 Drawing Sheets

(51) Int. Cl.
  *G01N 33/49* (2006.01)
  *G01N 21/64* (2006.01)
  *G01N 33/543* (2006.01)
(58) Field of Classification Search
  USPC .......................................................... 356/445
  See application file for complete search history.

(56) References Cited

U.S. PATENT DOCUMENTS

| | | | |
|---|---|---|---|
| 10,495,576 B2 * | 12/2019 | Matsuo | G01N 21/64 |
| 2014/0152801 A1 * | 6/2014 | Fine | G02B 21/0008 |
| | | | 348/79 |
| 2015/0060697 A1 * | 3/2015 | Umetsu | G02B 5/008 |
| | | | 250/458.1 |
| 2016/0299266 A1 * | 10/2016 | Umetsu | G02B 5/04 |
| 2016/0356717 A1 * | 12/2016 | Fujii | G01N 33/54373 |
| 2019/0151841 A1 * | 5/2019 | Iwashita | G01N 1/00 |
| 2019/0285545 A1 * | 9/2019 | Nagai | G01N 21/84 |
| 2020/0182784 A1 * | 6/2020 | Nagai | G01N 21/41 |
| 2020/0271593 A1 * | 8/2020 | Noda | G01N 21/648 |

* cited by examiner

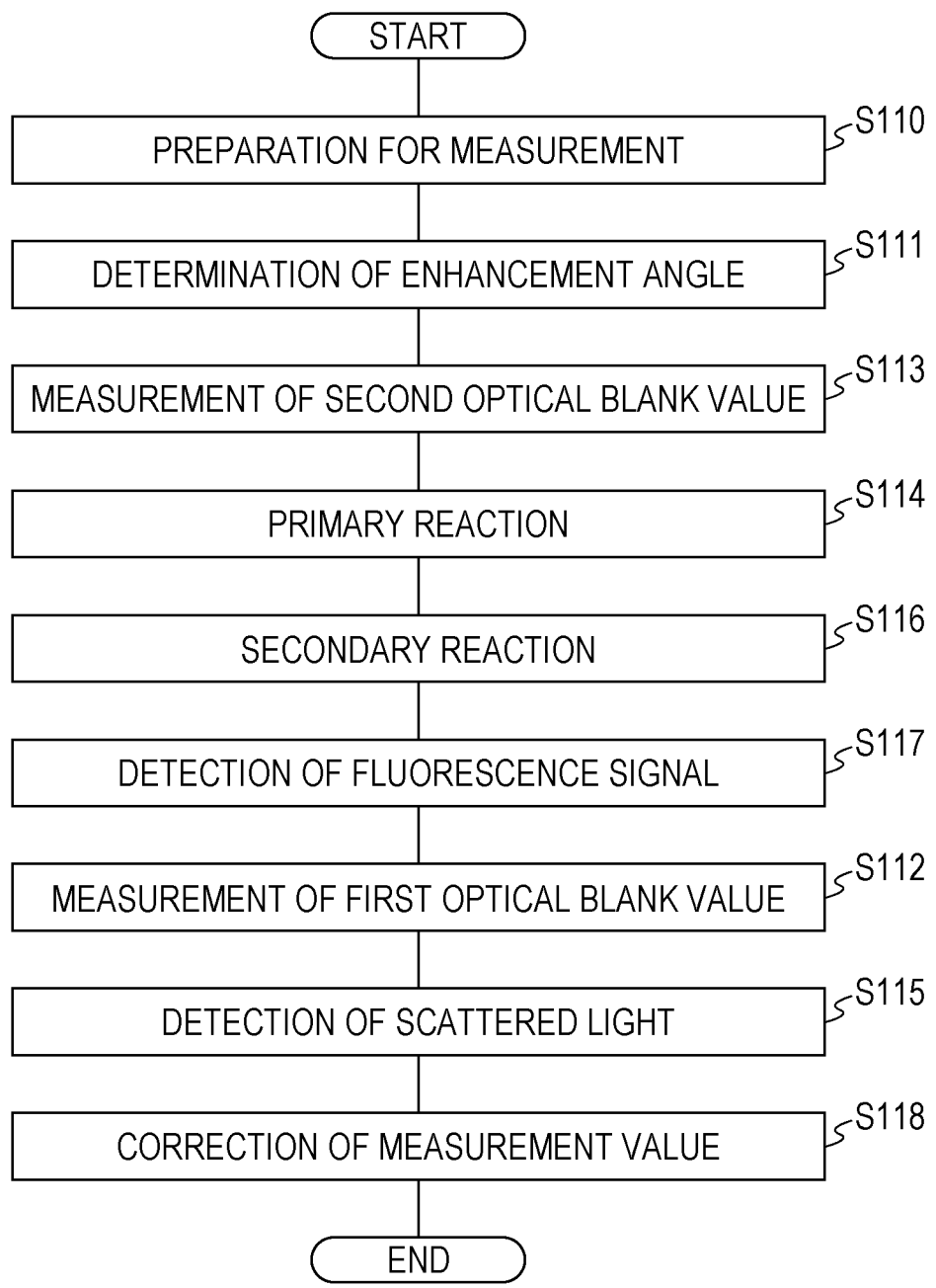

SURFACE PLASMON RESONANCE MEASUREMENT METHOD FOR MEASURING AMOUNT OF SUBSTANCE IN A SPECIMEN INCLUDING WHOLE BLOOD

CROSS REFERENCE TO RELATED APPLICATION

This Application is a 371 of PCT/JP2017/032132 filed on Sep. 6, 2017 which, in turn, claimed the priority of Japanese Patent Application No. 2016-179396 filed on Sep. 14, 2016, both applications are incorporated herein by reference.

TECHNICAL FIELD

The present invention relates to a measurement method for measuring an amount of a substance to be measured in a specimen including whole blood using surface plasmon resonance.

BACKGROUND ART

In clinical examinations, if it is possible to quantitatively measure a minute amount of substance to be measured such as protein and DNA in the blood with high sensitivity, it becomes possible to rapidly grasp a condition of a patient and treat. Therefore, a method capable of quantitatively measuring the substance to be measured in blood with high sensitivity is required.

As a method capable of measuring the substance to be measured in the blood with high sensitivity, a surface plasmon resonance (hereinafter abbreviated as "SPR") method and a surface plasmon-field enhanced fluorescence spectroscopy (hereinafter abbreviated as "SPFS") are known. In these methods, a fact that the surface plasmon resonance (SPR) occurs when light is applied to a metal film under a predetermined condition is used (refer to, for example, Patent Literatures 1 and 2). When the SPR occurs in the metal film, plasmon scattered light having the same wavelength as the light applied to the metal film is emitted from the vicinity of the metal film.

In the SPFS, a capturing body (for example, a primary antibody) capable of specifically binding to the substance to be measured is immobilized on the metal film to form a reaction field for specifically capturing the substance to be measured. When a specimen (for example, blood) containing the substance to be measured is provided in this reaction field, the substance to be measured is bound to the reaction field. Subsequently, when a capturing body (for example, a secondary antibody) labeled with a fluorescent substance is provided to the reaction field, the substance to be measured bound to the reaction field is labeled with the fluorescent substance. When the metal film is irradiated with excitation light in this state, the fluorescent substance that labels the substance to be measured is excited by an electric field enhanced by the SPR and emits fluorescence. Therefore, by detecting the fluorescence, presence or an amount of the substance to be measured may be detected. At that time, the plasmon scattered light is cut by an optical filter. In the SPFS, the fluorescent substance is excited by the electric field enhanced by the SPR, so that the substance to be measured may be measured with high sensitivity.

On the other hand, in a case of measuring the substance to be measured in liquid, a measurement value is usually indicated by a mass of the substance to be measured per unit volume of the liquid, a signal amount corresponding thereto and the like. Therefore, in a case of using the blood as the specimen, the measurement value is indicated by a mass of the substance to be measured per unit volume of a liquid component (plasma or serum) in the blood, a signal amount corresponding thereto and the like. Since a proportion of the liquid component in the blood varies among individuals, it is not possible to uniformly convert the measurement value of whole blood (blood) to the measurement value of the liquid component. Therefore, in a case of using the whole blood as the specimen, it is required to measure a hematocrit value (volume proportion of blood cells in the blood) of the whole blood and convert the measurement value of the whole blood to the measurement value of the liquid component (plasma or serum) using the hematocrit value.

As a conventional measurement method of the hematocrit value, there are a micro hematocrit method of centrifuging blood and an electric conduction method of obtaining the hematocrit value from electrical conductivity of blood. However, according to the conventional measurement method of the hematocrit value, it is necessary to newly prepare another device such as a centrifugal separator, a measurement device of electric conductivity, and a measurement device of the hematocrit value, and a manufacturing cost and a measurement cost of the measurement device increase.

On the other hand, in the measurement methods disclosed in Patent Literatures 1 and 2, the hematocrit value of the whole blood may be determined on the basis of a light amount of the plasmon scattered light generated in a measurement chip and scattered by the specimen when passing through the specimen when the excitation light is applied to the metal film at an incident angle equal to or larger than a critical angle. Therefore, according to the measurement method disclosed in Patent Literatures 1 and 2, it is not required to newly prepare a device for measuring the hematocrit value.

CITATION LIST

Patent Literature

Patent Literature 1: WO 2015/129615
Patent Literature 2: WO 2016/039149

SUMMARY OF INVENTION

Technical Problem

However, since intensity (light amount) of the plasmon scattered light is weak and correlation between the hematocrit value and the intensity of the plasmon scattered light is also weak, there is a room for improvement from a viewpoint of measuring the hematocrit value with a higher degree of accuracy in the measurement method of the hematocrit value disclosed in Patent Literatures 1 and 2.

An object of the present invention is to provide a measurement method using surface plasmon resonance, the measurement method capable of measuring a hematocrit value with a high degree of accuracy without newly preparing a device for measuring a hematocrit value and measuring an amount of a substance to be measured in a specimen including whole blood with a high degree of accuracy.

Solution to Problem

In order to solve the above-described problem, a measurement method according to an embodiment of the present invention is a measurement method for measuring an amount of a substance to be measured in a specimen including whole blood using surface plasmon resonance, the measurement method provided with a step of preparing a measurement chip including a prism including an incident surface and a film depositing surface, a metal film arranged on the film depositing surface, and a capturing body immobilized on the metal film, a step of detecting scattered light obtained when first light passing through the metal film and the specimen is scattered in the specimen when the first light is applied to the metal film at a first incident angle smaller than a critical angle from a prism side in a state in which the specimen is present on the metal film, a step of detecting a signal indicating the amount of the substance to be measured generated in the measurement chip when second light is applied to the metal film at a second incident angle equal to or larger than the critical angle from the prism side in a state in which the substance to be measured is captured by the capturing body and the specimen is not present on the metal film, and a step of correcting a measurement value indicating the amount of the substance to be measured determined from the detected signal on the basis of a hematocrit value of the specimen determined from a light amount of the detected scattered light.

Advantageous Effects of Invention

According to the present invention, it is possible to measure a hematocrit value with a high degree of accuracy without newly adding a device for hematocrit value measurement in a measurement method using surface plasmon resonance. Therefore, according to the present invention, it is possible to measure an amount of a substance to be measured in a specimen including whole blood with a high degree of accuracy without increasing a manufacturing cost and a measuring cost of a measurement device.

BRIEF DESCRIPTION OF DRAWINGS

FIG. 9 is a flowchart illustrating an example of a measurement method according to a variation.

DESCRIPTION OF EMBODIMENTS

An embodiment of the present invention is hereinafter described in detail with reference to the drawings. A measurement method according to the present invention is a measurement method for measuring an amount of a substance to be measured in a specimen containing whole blood using surface plasmon resonance. Herein, as a representative example of the measurement method according to the present invention, a measurement method using surface plasmon-field enhanced fluorescence spectroscopy (hereinafter abbreviated as "SPFS") is described. In the measurement method according to this embodiment, fluorescence emitted from a fluorescent substance which labels the substance to be measured is detected as a signal indicating the amount of the substance to be measured.

Figure 1:
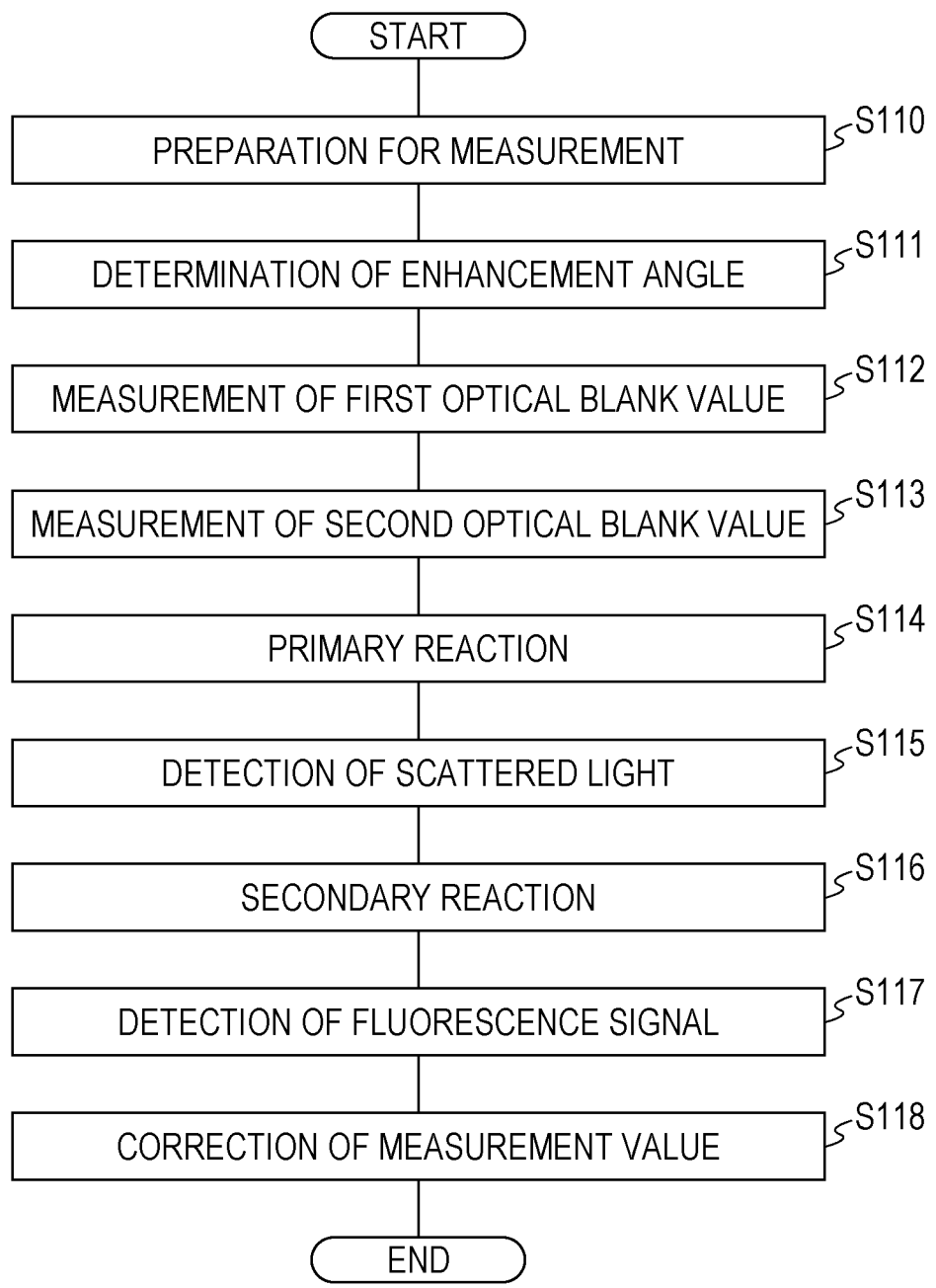
FIG. 1 is a flowchart illustrating an example of a measurement method according to an embodiment of the present invention.
Figure 2:
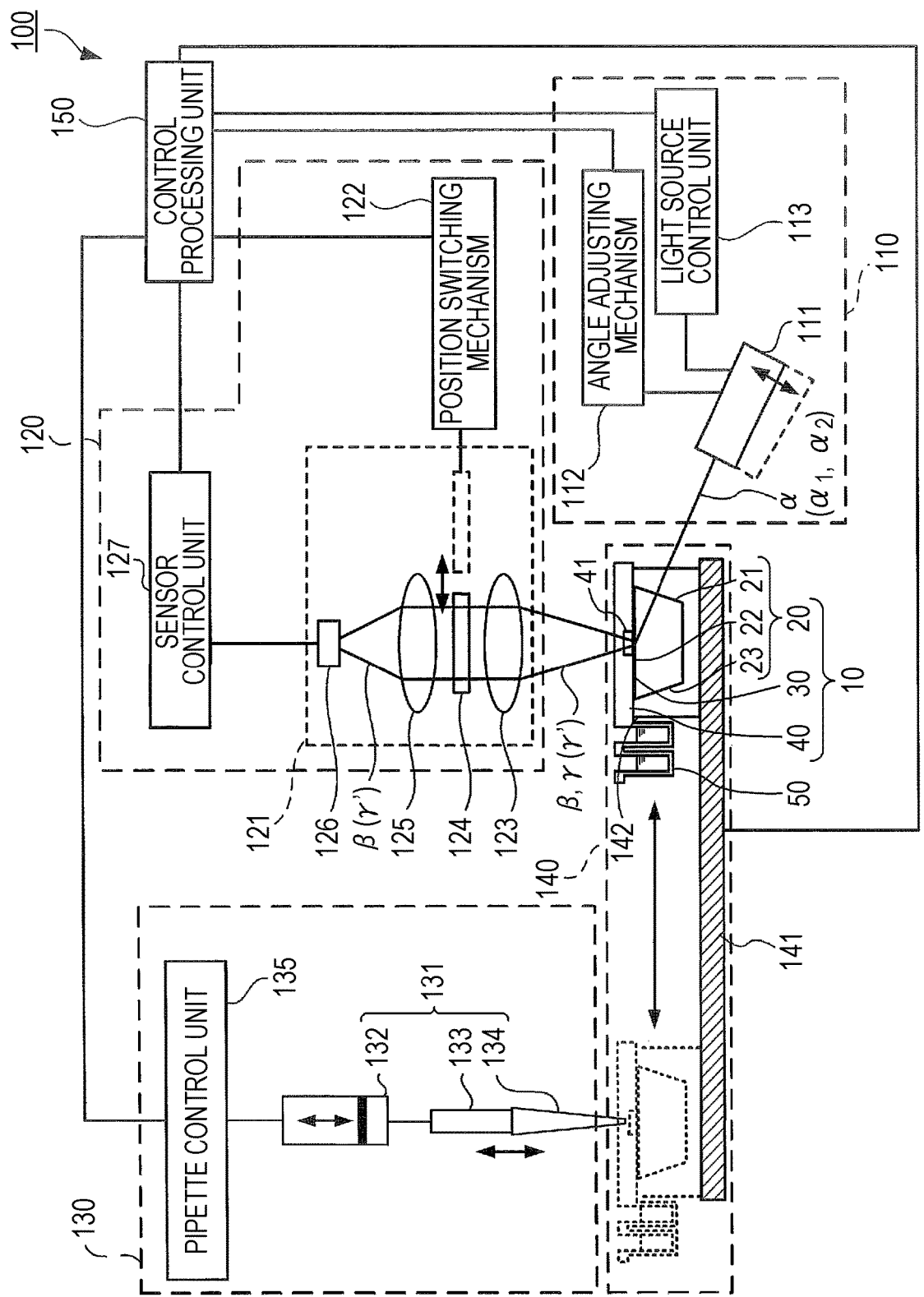
FIG. 2 is a view illustrating an example of configurations of a measurement chip and a measurement device (SPFS device) which might be used for implementing the measurement method according to an embodiment of the present invention.

FIG. 1 is a flowchart illustrating an example of the measurement method according to a first embodiment. FIG. 2 is a view illustrating an example of configurations of a measurement chip 10 and a measurement device (SPFS device) 100 which might be used for implementing the measurement method according to the first embodiment. The measurement chip 10 and the SPFS device 100 are separately described in detail.

The measurement method according to this embodiment includes a step of preparing measurement (step S110), a step of determining an enhancement angle (step S111), a step of measuring a first optical blank value (step S112), a step of measuring a second optical blank value (step S113), a step of performing a primary reaction (step S114), a step detecting scattered light (step S115), a step of performing a secondary reaction (step S116), a step of detecting a fluorescence signal (step S117), and a step of correcting a measurement value (step S118).

1) Preparation for Measurement

First, the measurement is prepared (step S110). Specifically, the measurement chip 10 is prepared and the measurement chip 10 is installed in a chip holder 142 arranged in an installation position of the SPFS device 100. Herein, the "installation position" is a position for installing the measurement chip 10 on the SPFS device 100.

(Measurement Chip)

The measurement chip 10 used in the SPFS device 100 is herein described. As illustrated in FIG. 2, the measurement chip 10 includes a prism 20, a metal film 30, and a flow path lid 40. In this embodiment, the flow path lid 40 of the measurement chip 10 is integrated with a liquid chip 50 for accommodating liquid.

The prism 20 includes an incident surface 21, a film depositing surface 22, and an emission surface 23. The incident surface 21 allows emission light α from a light emitting unit 110 to be described later to enter the prism 20. The metal film 30 is arranged on the film depositing surface 22. The emission surface 23 emits reflected light entering the prism 20 from the incident surface 21 to be reflected by an interface (film depositing surface 22) between the prism 20 and the metal film 30 out of the prism 20.

A shape of the prism 20 is not especially limited. In this embodiment, the shape of the prism 20 is a columnar body having a trapezoid as a bottom surface. A surface corresponding to one bottom side of the trapezoid is the film depositing surface 22, a surface corresponding to one leg is the incident surface 21, and a surface corresponding to the other leg is the emission surface 23.

The incident surface 21 is formed such that the emission light α from the light emitting unit 110 is not reflected by the incident surface 21 to return to a light source of the SPFS device 100. In a case where the light source of the emission light α is a laser diode (hereinafter also referred to as "LD"), when the emission light α returns to the LD, an excited state of the LD is disturbed and a wavelength and an output of the emission light α fluctuate. Therefore, an angle of the incident surface 21 is set such that the emission light α does not incident on the incident surface 21 perpendicularly in a scanning range centered on an ideal resonance angle or enhancement angle.

Herein, the "resonance angle" means an incident angle when a light amount of the reflected light of the emission light α emitted from the emission surface 23 becomes the minimum in a case when the incident angle of the emission light α with respect to the metal film 30 is scanned. In addition, the "enhancement angle" means the incident angle when a light amount of scattered light (hereinafter referred to as "plasmon scattered light") γ having the same wavelength as that of the emission light α emitted above the measurement chip 10 becomes the maximum in a case where the incident angle of the emission light α with respect to the metal film 30 is scanned. In this specification, the light emitted above the measurement chip 10 when the incident angle of the emission light α with respect to the metal film 30 is not smaller than a critical angle is referred to as the "plasmon scattered light γ". Also, the light emitted above the measurement chip 10 when the incident angle of the emission light α with respect to the metal film 30 is smaller than the critical angle is referred to as "scattered light γ'". In this embodiment, an angle between the incident surface 21 and the film depositing surface 22 and an angle between the film depositing surface 22 and the emission surface 23 are both approximately 80 degrees.

Note that the resonance angle (and the enhancement angle in the close vicinity thereof) is roughly determined by a design of the measurement chip 10. Design elements are a refractive index of the prism 20, a refractive index of the metal film 30, a thickness of the metal film 30, an extinction coefficient (extinction coefficient) of the metal film 30, the wavelength of the emission light α and the like. The resonance angle and the enhancement angle are shifted by the substance to be measured captured on the metal film 30, but an amount thereof is smaller than several degrees.

The prism 20 is made of a dielectric body transparent to the emission light α. The prism 20 has a birefringence characteristic more than little. Examples of a material of the prism 20 include resin and glass. Examples of the resin forming the prism 20 include polymethylmethacrylate (PMMA), polycarbonate (PC), and cycloolefin polymer. The material of the prism 20 is preferably resin having the refractive index of 1.4 to 1.6 and small birefringence.

The metal film 30 is arranged on the film depositing surface 22 of the prism 20. As a result, surface plasmon resonance (hereinafter abbreviated as "SPR") occurs between photons of the emission light α incident on the film depositing surface 22 under a total reflection condition and free electrons in the metal film 30, and it is possible to generate localized field light (generally also referred to as "evanescent light" or "near field light") on a surface of the metal film 30. The localized field light reaches a distance approximately the wavelength of the emission light α from the surface of the metal film 30. The metal film 30 may be formed on an entire surface on the film depositing surface 22 or formed on a part of the film depositing surface 22. In this embodiment, the metal film 30 is formed on the entire surface of the film depositing surface 22.

On the metal film 30, a capturing body for capturing the substance to be measured is immobilized. On the metal film 30, a region in which the capturing body is immobilized is especially referred to as a "reaction field". The capturing body may be immobilized on an entire surface of the metal film 30 or may be immobilized on a part of the surface. The capturing body specifically binds to the substance to be measured. Therefore, the substance to be measured might be immobilized on the metal film 30 via the capturing body.

A type of the capturing body is not especially limited as long as this may capture the substance to be measured. For example, the capturing body is an antibody (primary antibody) capable of specifically binding to the substance to be measured, a fragment thereof, an enzyme capable of specifically binding to the substance to be measured or the like.

The material of the metal film 30 is not especially limited as long as this may cause the surface plasmon resonance (SPR) and transmit at least a part of the emission light α. Examples of the material of the metal film 30 include gold, silver, copper, and alloys thereof. The thickness of the metal film 30 is preferably 30 to 60 nm from a viewpoint of efficiently generating the SPR and obtaining a desired transmittance with respect to the emission light α. The transmittance of the metal film 30 with respect to the emission light α is, for example, 3 to 30% when P-polarized light is applied to the metal film 30 at the incident angle of 50 degrees.

Also, the thickness of the metal film 30 may be appropriately set according to the material from the above-described viewpoint. For example, in a case where the material of the metal film 30 is gold, the thickness of the metal film 30 is preferably 30 to 55 nm in order to set the transmittance to 5 to 30% (refer to reference experiment 3 to be described later). Also, in a case where the material of the metal film 30 is silver, the thickness of the metal film 30 is preferably 35 to 60 nm in order to set the transmittance to 3 to 20%. Furthermore, in a case where the material of the metal film 30 is copper, the thickness of the metal film 30 is preferably 30 to 55 nm in order to set the transmittance to 5 to 25%. Among the above-described materials, the material of the metal film 30 is preferably gold. This is because gold having higher transmittance than other metals may cause the SPR with high efficiency and has high stability (for example, oxidation resistance) to an external environment. In this embodiment, the metal film 30 is a gold thin film. The method of forming the metal film 30 is not especially limited. Examples of the method of forming the metal film 30 include sputtering, vapor deposition, and plating.

The flow path lid 40 is arranged on the metal film 30. In a case where the metal film 30 is formed only on a part of the film depositing surface 22 of the prism 20, the flow path lid 40 may also be arranged on the film depositing surface 22. In this embodiment, the flow path lid 40 is arranged on the metal film 30. By arranging the flow path lid 40 on the metal film 30, an accommodating unit for accommodating the liquid is formed on the metal film 30. In this embodiment, the accommodating unit is a flow path 41 through which the liquid flows. The flow path 41 includes a bottom surface, a top surface, and a pair of side surfaces connecting the bottom surface and the top surface. In this specification, a surface of the flow path 41 on the prism 20 side is referred to as the bottom surface of the flow path, and a surface of the flow path 41 opposed to the bottom surface of the flow path 41 is referred to as the top surface of the flow path. Also, an interval between the bottom surface of the flow path 41 and the top surface of the flow path 41 is set as a height of the flow path 41.

A recess (flow path groove) is formed on a rear surface of the flow path lid 40. The flow path lid 40 is arranged on the metal film 30 (and the prism 20), and an opening of the recess is closed by the metal film 30, so that the flow path 41 is formed. From a viewpoint of sufficiently securing a region where the localized field light reaches, it is preferable that the height of the flow path 41 (depth of the flow path groove) is large to some extent. From a viewpoint of reducing an amount of impurities mixed in the flow path 41, the height of the flow path 41 (the depth of the flow path groove) is preferably small. From such a viewpoint, the height of the flow path 41 is preferably in a range from 0.05 to 0.15 mm. Both ends of the flow path 41 are connected to an injection port and a discharge port not illustrated formed on the flow path lid 40 so as to allow an inside and an outside of the flow path 41 to communicate with each other.

The flow path lid 40 is preferably formed of a material transparent to the light (fluorescence β, scattered light γ', and plasmon scattered light γ) emitted from an upper side of the metal film 30. Examples of a material of the flow path lid 40 include glass and resin. Examples of the resin include polymethylmethacrylate resin (PMMA). Also, the other part of the flow path lid 40 may be formed of an opaque material as long as this is transparent to the above-described light. The flow path lid 40 is joined to the metal film 30 or the prism 20 by, for example, bonding with a double-sided tape, an adhesive and the like, laser welding, ultrasonic welding, crimping using a clamp member and the like.

Note that a flow path lid in which a recess (flow path groove) is not formed on a rear surface may also be used in place of the above-described flow path lid 40. In this case, the flow path lid without the recess and the metal film 30 or the prism 20 are joined by using a double-sided tape having a thickness of 0.05 to 0.15 mm in which a through hole serving as a flow path is formed in a central portion thereof. The flow path 41 may also be formed in this manner.

The measurement chip 10 is usually replaced for each measurement. Also, the measurement chip 10 is preferably a structure a length of each piece of which is several millimeters to several centimeters, but this may also be a smaller structure or a larger structure not included in a category of "chip".

Note that, at the step of preparing the measurement (step S110), in a case where a stored reagent is present on the metal film 30 of the measurement chip 10, the stored reagent is removed by washing the metal film 30 so that the capturing body may appropriately capture the substance to be measured.

2) Determination of Enhancement Angle

Next, the enhancement angle is determined (step S111). Specifically, first, measuring liquid is injected into the flow path 41. For example, the measuring liquid is provided into the flow path 41 by using a pipette 131 to be described later. It is only required that the measuring liquid is transparent to the emission light α, and this is, for example, a buffer solution such as phosphate buffered saline (PBS), Tris buffered saline with Tween 20 (TBS-T), HEPES buffered saline (HBS).

Next, in a state in which the measuring liquid is present in the flow path 41, the emission light α is applied to the rear surface of the metal film 30 corresponding to the region in which the capturing body is immobilized via the prism 20 while scanning the incident angle of the emission light α with respect to the metal film 30, and the plasmon scattered light γ generated in the measurement chip 10 is detected. In this embodiment, the incident angle of the emission light α from the light source unit 111 with respect to the metal film 30 is scanned by an angle adjusting mechanism 112, and the plasmon scattered light γ is detected by a light receiving sensor 126. As a result, data including a relationship between the incident angle of the emission light α with respect to the metal film 30 and the light amount of the plasmon scattered light γ is obtained. By analyzing the obtained data, the enhancement angle which is the incident angle at which the light amount of the plasmon scattered light γ becomes the maximum is determined. Note that, at this step, an optical filter 124 (to be described later) which transmits only the fluorescence β component and removes an emission light α component (scattered light γ' and plasmon scattered light γ) is arranged so as to be located outside the optical path of the plasmon scattered light γ partially or entirely. As a result, the emission light α component enters the light receiving sensor 126.

Note that the enhancement angle is determined by the material and shape of the prism 20, the thickness of the metal film 30, the refractive index of the liquid in the flow path 41 and the like, but this slightly fluctuates by various factors such as the type and amount of the capturing body in the flow path 41, an error in shape of the prism 20, and an installation error of the measurement chip 10 in the SPFS device 100. Therefore, it is preferable to determine the enhancement angle each time the measurement is performed. The enhancement angle is determined on the order of approximately 0.1 degree.

3) Measurement of First Optical Blank Value

Next, the first optical blank value is measured (step S112). Herein, the first optical blank value is the optical blank value used when determining a hematocrit value and this means a light amount of light having the same wavelength as that of the emission light α emitted above the measurement chip 10 when the emission light α is applied to the metal film 30 at a predetermined first incident angle smaller than the critical angle in a state in which the measuring liquid is present in the flow path 41. Hereinafter, the emission light α applied to the metal film 30 at the first incident angle is also referred to as "first emission light $α_1$ (referred to as "first light" in claims)".

At this step, first, the first emission light $α_1$ is applied to the metal film 30 at the first incident angle smaller than the critical angle, and the light emitted above the measurement chip 10 is detected. Although it is described in detail later, it is sufficient that the first incident angle is smaller than the critical angle, and from a viewpoint of measuring the hematocrit value with a high degree of accuracy and suppressing an increase in size of the SPFS device 100, the first incident angle is preferably smaller to some extent than the critical angle (for example, about 5 to 10 degrees). Also, in this embodiment, the light emitted above the measurement chip 10 is detected by the light receiving sensor 126 while applying the first emission light $α_1$ from the light source unit 111 to the metal film 30 at the first incident angle. As a result, the first optical blank value which is a light amount of light which becomes noise in the detection of the scattered light γ' (step S115) is obtained. Note that, at this step also, the optical filter 124 is arranged so as to be located outside the optical path partially or entirely.

4) Measurement of Second Optical Blank Value

Next, the second optical blank value is measured (step S113). Herein, the second optical blank value is the optical blank value used when determining the amount of the substance to be measured and this means the light amount of the light of the same wavelength as that of the emission light α emitted above the measurement chip 10 when the emission light α is applied to the metal film 30 at a predetermined second incident angle not smaller than the critical angle in a state in which the measuring liquid is present in the flow path 41. Hereinafter, the emission light α applied to the metal film 30 at the second incident angle is also referred to as "second emission light $α_2$ (referred to as "second light" in claims)".

At this step, first, the incident angle of the emission light α with respect to the metal film 30 (film depositing surface 22) is switched to the second incident angle. It is sufficient that the second incident angle is equal to or larger than the critical angle, and this is an angle for causing the SPR on the metal film 30 irradiated with the emission light α. In this embodiment, the light source in the light source unit 111 is rotated to switch from the first incident angle to the enhancement angle (second incident angle) determined at step S111. Next, the second emission light $\alpha_2$ is applied to the metal film 30 at the enhancement angle, and the light emitted above the measurement chip 10 is detected. In this embodiment, the light emitted above the measurement chip 10 is detected by the light receiving sensor 126 while applying the second emission light $\alpha_2$ from the light source unit 111 to the metal film 30 at the enhancement angle. As a result, the second optical blank value which is a light amount of light which becomes noise in the detection of the fluorescence signal (step S117) is obtained. Note that, at this step, the optical filter 124 is arranged on the optical path.

5) Primary Reaction

Next, the substance to be measured in the specimen and the capturing body on the metal film 30 are allowed to react (primary reaction; step S114). Specifically, first, the measuring liquid is removed from the flow path 41, and the specimen is injected into the flow path 41. For example, after sucking the measuring liquid in the flow path 41 by using the pipette 131, the specimen is provided in the flow path 41. As a result, in a case where the substance to be measured is present in the specimen, at least a part of the substance to be measured might be captured by the capturing body on the metal film 30.

The specimen contains whole blood and may be diluted as necessary. From a viewpoint of measuring the scattered light γ' with high intensity at step S115 to be described later, it is preferable that concentration of the specimen is high. This is because, the higher the concentration of the specimen, the larger the amount of light scattered in the specimen and the larger the light amount of scattered light γ' detected. On the other hand, from a viewpoint of measuring the fluorescence β with high accuracy at step S117 to be described later, it is preferable that the concentration of the specimen is low to a certain degree. This is because, when the concentration of the specimen is low to a certain degree, an amount of absorption (nonspecific adsorption) of impurities in the specimen to the capturing body may be decreased and the noise may be decreased. Also, by adjusting the amount of the substance to be measured relative to the amount of the capturing body within an appropriate range, saturation of the amount of the substance to be captured which may be captured by the capturing body may be suppressed. As a diluent, for example, physiological saline might be used. Examples of the substance to be measured in the whole blood include troponin, myoglobin, and creatine kinase-MB (CK-MB).

6) Detection of Scattered Light

Next, the scattered light γ' indicating the hematocrit value of the specimen is detected (step S115). Specifically, the scattered light γ' obtained when the first emission light $\alpha_1$ which passes through the metal film 30 and the specimen is scattered in the specimen when the first emission light $\alpha_1$ is applied to the metal film 30 from the prism 20 side at the first incident angle is detected. More specifically, the scattered light γ' is obtained when the first emission light $\alpha_1$ is scattered by a blood cell component in the specimen. In this embodiment, the scattered light γ' is detected by the light receiving sensor 126 while applying the emission light α from the light source unit 111 to the metal film 30 at the first incident angle. This makes it possible to measure the light amount of scattered light γ' indicating the hematocrit value of the specimen. Note that, at this step, the optical filter 124 is arranged so as to be located outside the optical path of the scattered light γ' partially or entirely.

At this step, the first emission light $\alpha_1$ is the light having the same wavelength and light amount as the emission light α applied to the metal film 30 at step S112. The first emission light $\alpha_1$ applied to the metal film 30 is preferably the P-polarized light having a wavelength of 600 to 700 nm. When the wavelength of the first emission light $\alpha_1$ is 600 to 700 nm, the transmittance of the first emission light $\alpha_1$ to the gold film (metal film 30) increases and it is possible to suppress the scattered light γ' from being absorbed by hemoglobin in the specimen. As a result of them, the light amount of the scattered light γ' detected by the light receiving sensor 126 may be increased. In addition, since the first emission light $\alpha_1$ is the P-polarized light, the transmittance of the first emission light $\alpha_1$ with respect to the metal film 30 is further increased, so that the light amount of the detected scattered light γ' may be increased. As a result of them, the hematocrit value may be determined with a high degree of accuracy.

At this step, from a viewpoint of increasing the light amount of the scattered light γ' obtained when the first emission light $\alpha_1$ is scattered in the specimen and determining the hematocrit value with a high degree of accuracy, it is preferable that the concentration of the specimen is high. For example, the specimen is preferably the whole blood having a dilution ratio of one to 10 times, and is more preferably the whole blood having the dilution ratio of one to three times (refer to reference experiment 2 to be described later). In this embodiment, the specimen is the whole blood having the dilution ratio of one to 10 times.

Also, as described above, from a viewpoint of determining the hematocrit value with a high degree of accuracy, it is preferable that the first incident angle is smaller to some extent than the critical angle. For example, it is preferable that the first incident angle is equal to or smaller than an angle smaller than the critical angle by five degrees (refer to simulation to be described later). Furthermore, from a viewpoint of shortening a switching time between the first incident angle and the second incident angle and reducing a size of the SPFS device 100 by reducing the difference between the first incident angle and the second incident angle, the difference between the first incident angle and the second incident angle is preferably small. For example, the first incident angle is more preferably equal to or smaller than the angle smaller than the critical angle by five degrees or equal to or larger than the angle smaller than the critical angle by 10 degrees.

Note that although the example in which the scattered light γ' is detected (step S115) after the primary reaction (step S114) is finished is heretofore described, it is also possible that the scattered light γ' is detected after the primary reaction starts and before this ends. For example, it is possible to detect the scattered light γ' immediately after injecting the specimen into the flow path 41 after the primary reaction step is started, and thereafter perform remaining primary reaction until a reaction time of the primary reaction reaches a predetermined time. There is a possibility that red blood cells settle down while reciprocating the specimen in the flow path 41 in the primary reaction and it is not possible to accurately detect the scattered light γ'; however, this method is preferable because the scattered light γ' may be detected before the red blood cells settle down. This method is especially effective in a case where the red blood cells easily settle down such as a case where the reaction time of the primary reaction is long, the dilution ratio of the specimen is high, and the hematocrit value is low. Of course, also in a case where the scattered light γ' is detected prior to the primary reaction, the primary reaction itself is started when the specimen is injected into the flow path 41, and the substance to be measured in the specimen and the capturing body on the metal film 30 come into contact with each other. However, in a case of detecting the scattered light γ' in the middle of the primary reaction, from a viewpoint of accurately measuring the intensity of the scattered light γ', when detecting the scattered light γ', it is preferable to stop movement of fluid in the flow path 41, that is, to stop sending the liquid. In either case, since the primary reaction may be performed in parallel with the detection of the scattered light γ', a total measuring time may be shortened and the type of the specimen to be prepared may be made one, so that the procedure becomes simple.

7) Secondary Reaction

Subsequently, the substance to be measured captured by the capturing body on the metal film 30 is labeled with the fluorescent substance (secondary reaction; step S116). Specifically, after removing the specimen from the flow path 41 by the pipette 131, the interior of flow path 41 is washed with the buffer solution and the like to remove substances not captured by the capturing body. Next, a fluorescent labeling solution is provided in the flow path 41 by the pipette 131. As a result, the substance to be measured may be labeled with the fluorescent substance. The fluorescent labeling solution is, for example, a buffer solution containing an antibody (secondary antibody) labeled with the fluorescent substance. Thereafter, the interior of the flow path 41 is washed with the buffer solution and the like to remove free fluorescent substances and the like.

8) Detection of Fluorescence Signal

Next, fluorescence β (signal) indicating the amount of the substance to be measured is detected (step S117). Specifically, the fluorescence β (signal) indicating the amount of the substance to be measured generated in the measurement chip 10 when the second emission light $α_2$ is applied to the rear surface of the metal film 30 corresponding to the region in which the capturing body is immobilized via the prism 20 at the enhancement angle (second incident angle) from the prism 20 side in a state in which the substance to be measured is captured by the capturing body on the metal film 30 and there is no specimen (state in which the flow path 41 is filled with the measuring liquid) is detected. At that time, the second emission light $α_2$ is excitation light which may excite the fluorescent substance directly or indirectly. In this embodiment, the fluorescence β is detected by the light receiving sensor 126 while applying the emission light α from the light source unit 111 to the metal film 30 such that the second incident angle becomes the enhancement angle. As a result, it is possible to measure a fluorescence value which is the light amount of the fluorescence β indicating the amount of the substance to be measured in the specimen with high intensity. Note that, at this step, the optical filter 124 is arranged on the optical path.

In this specification, a "state in which no specimen is present" means a state in which operation of removing the specimen from the flow path 41 is performed. That is, it suffices that there is substantially no specimen in the flow path 41, and a small amount of specimen which cannot be removed may be left in the flow path 41.

At this step, the second emission light $α_2$ is light having the same wavelength as that of the emission light α applied to the metal film 30 at steps S111 and S113. The second emission light $α_2$ is light of a wavelength which might excite the fluorescent substance which labels the substance to be measured. The wavelength and light amount of the second emission light $α_2$ may be the same as or different from the wavelength and the light amount of the first emission light $α_1$. From a viewpoint of making the measurement device small by using the same light source, it is preferable that the wavelength and the light amount of the second emission light $α_2$ are the same as the wavelength and the light amount of the first emission light $α_1$. In this embodiment, the wavelength and the light amount of the second emission light $α_2$ are the same as the wavelength and the light amount of the first emission light $α_1$.

9) Correction of Measurement Value

Next, the measurement value is corrected (step S118). Specifically, the measurement value indicating the amount of the substance to be measured determined from the fluorescence β detected at step S117 is corrected on the basis of the hematocrit value of the specimen determined from the light amount of the scattered light γ' detected at step S115.

First, the hematocrit value of the specimen is determined from the light amount of the scattered light γ'. The scattered light γ' includes a scattering component (signal component) resulting from the scattering in the specimen and a noise component (first optical blank value) caused by the scattering in the region other than the specimen (for example, the prism 20, the metal film 30, and the flow path lid 40). Therefore, by subtracting the first optical blank value obtained at step S112 from the light amount of the scattered light γ' detected at step S115, the scattering component (signal component) in the specimen may be calculated. Next, the hematocrit value of the specimen may be determined on the basis of a calibration curve indicating a relationship between the signal component and the light amount of the scattered light γ' and the hematocrit value.

Next, the measurement value indicating the amount (concentration) of the substance to be measured in the specimen is determined from the fluorescence value which is the light amount of the fluorescence β. The fluorescence value includes the fluorescent component (signal component) derived from the fluorescent substance which labels the substance to be measured and the noise component (second optical blank value) caused by a factor other than the fluorescent substance. Therefore, by subtracting the second optical blank value obtained at step S113 from the fluorescence value obtained at step S117, it is possible to calculate the measurement value (signal component) indicating the amount of the substance to be measured in the specimen.

Finally, the measurement value indicating the amount of the substance to be measured in the specimen is corrected on the basis of the hematocrit value. Specifically, by multiplying the measurement value by a conversion coefficient c expressed by following equation (1), this is converted into the amount of the substance to be measured in plasma.

[Equation 1]

$$c = \frac{(df-1) + \left(1 - \frac{Hct}{100}\right)}{df\left(1 - \frac{Hct}{100}\right)} \quad (1)$$

[In equation (1) above, Hct represents the hematocrit value (0 to 100%), and df represents the dilution ratio of the specimen.]

By the above-described procedure, the amount (concentration) of the substance to be measured in the plasma may be determined.

(Simulation)

Simulation was performed to investigate a preferable range of the incident angle of the emission light α with respect to the metal film 30 when detecting the scattered light γ' to determine the hematocrit value. Specifically, with respect to the metal films 30 having different thicknesses, a simulation was performed on a relationship between the incident angle of the emission light α with respect to the metal film 30 and reflectance (transmittance) of the emission light α. In this simulation, the wavelength of the emission light α was set to 660 nm, the refractive index of the prism 20 was set to 1.528, the refractive index of the metal film 30 was set to 0.2144, the extinction coefficient of the metal film 30 was set to 3.85, and the refractive index of the specimen was set to 1.331.

Figure 3A:
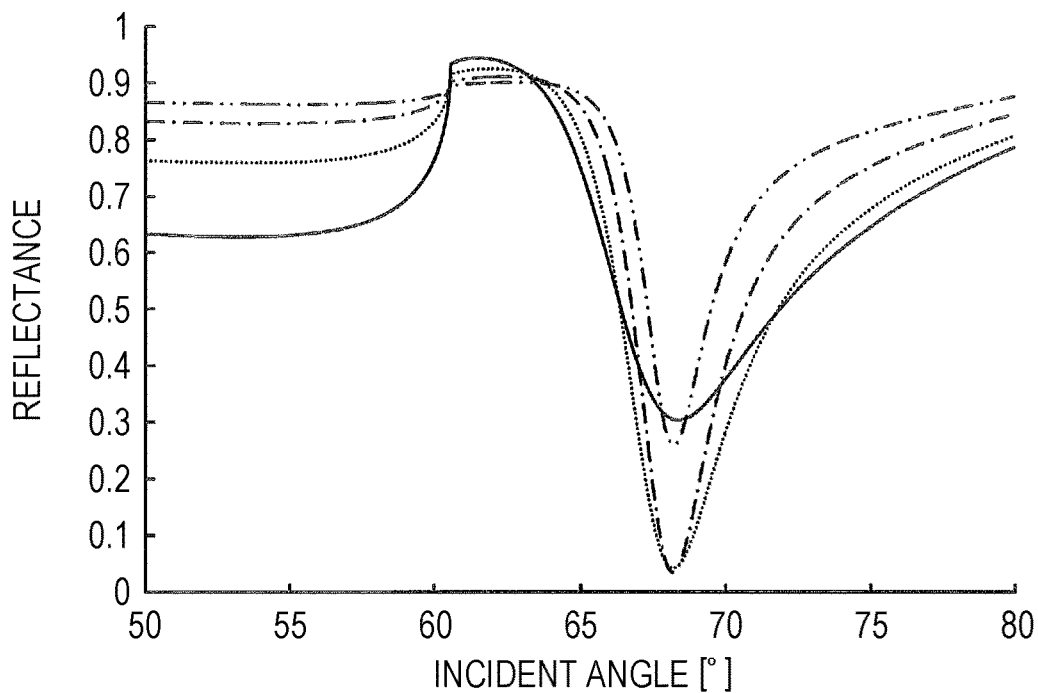
FIGS. 3A and 3B are graphs illustrating results of simulation.
Figure 3B:
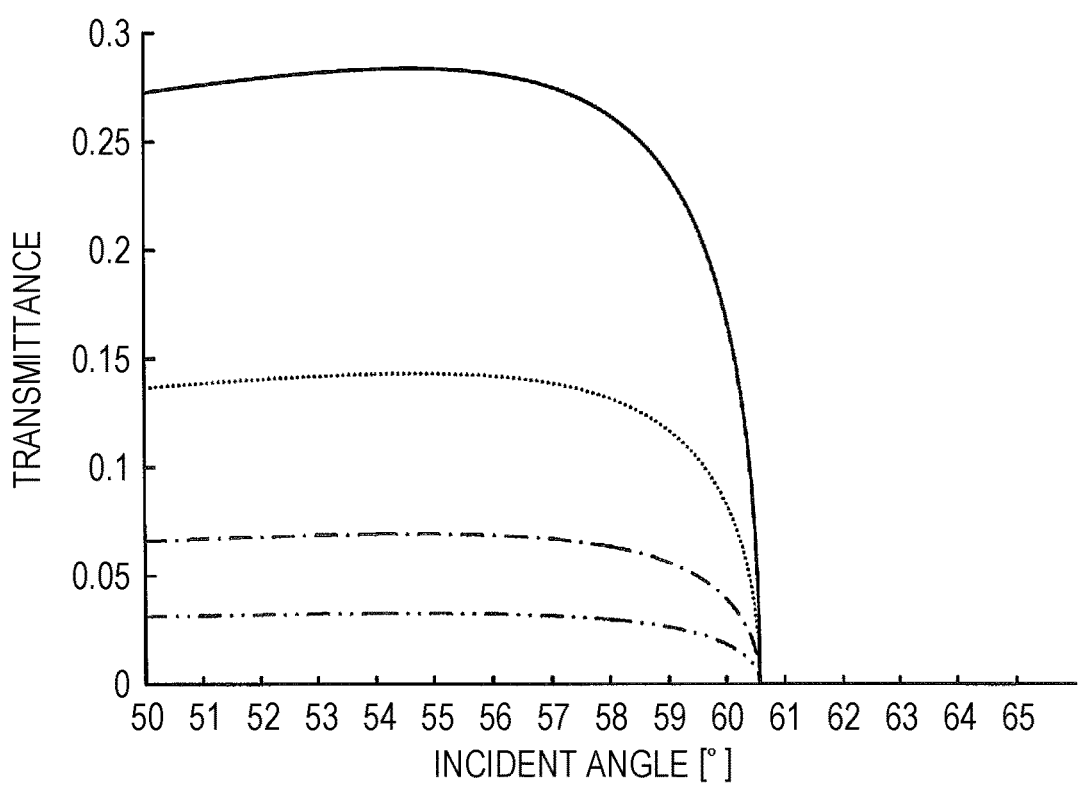

FIGS. 3A and 3B are graphs illustrating results of the simulation. FIG. 3A is a graph illustrating the relationship between the incident angle of the emission light α and the reflectance of the emission light α with respect to the metal film 30, and FIG. 3B is a graph illustrating the relationship between the incident angle of the emission light α and the transmittance of the emission light α with respect to the metal film 30. In FIG. 3A, the incident angle (°) of the emission light α with respect to the metal film 30 is plotted along the horizontal axis, and the reflectance of the emission light α with respect to the metal film 30 is plotted along the vertical axis. In FIG. 3B, the incident angle (°) of the emission light α with respect to the metal film 30 is plotted along the horizontal axis, and the transmittance of the emission light α with respect to the metal film 30 is plotted along the vertical axis. In FIGS. 3A and 3B, the simulation result when the thickness of the metal film 30 is 30 nm is indicated by a solid line, the simulation result when the thickness of the metal film 30 is 40 nm is indicated by a dotted line, the simulation result when the thickness of the metal film 30 is 50 nm is indicated by a dashed-dotted line, and the simulation result when the thickness of the metal film 30 is 60 nm is indicated by a dashed-two dotted line.

As illustrated in FIG. 3A, the reflectance of the emission light α with respect to the metal film 30 decreases as the incident angle of the emission light α decreases in a region in which the incident angle is from about 55 degrees to about 60.5 degrees (critical angle). At that time, it is understood that a change amount of the reflectance increases as the incident angle is closer to the critical angle, and decreases as the incident angle is away from the critical angle. It is also understood that the reflectance hardly changes in the region in which the incident angle is about 55 degrees or smaller.

In addition, as illustrated in FIG. 3B, the transmittance of the emission light α increases as the incident angle of the emission light α decreases in the region in which the incident angle is from about 55 degrees to about 60.5 degrees (critical angle). At that time, it is understood that a change amount of the transmittance increases as the incident angle is closer to the critical angle, and decreases as the incident angle is away from the critical angle. It is also understood that the transmittance hardly changes in the region in which the incident angle is about 55 degrees or smaller.

From the results of this simulation, it is understood that the scattered light γ' is preferably detected in the region in which the change in the reflectance (transmittance) may be suppressed even if the incident angle of the emission light α changes in order to determine the hematocrit value with a high degree of accuracy. From such a viewpoint, the first incident angle is preferably equal to or smaller than the angle smaller than the critical angle by five degrees. As a result, it is possible to suppress a change in an amount of the emission light α transmitted through the metal film 30 caused by a change in the critical angle due to slight deviation in the refractive index of the liquid in the flow path 41 (for example, Δn=0.001), slight deviation in the incident angle of the emission light α (for example, 0.1°) and the like. As a result, it is possible to suppress the change in the light amount of the detected scattered light γ' and to determine the hematocrit value with a high degree of accuracy.

(Reference Experiment 1)

An experiment for comparing the light amount of the scattered light γ' with the light amount of the plasmon scattered light γ and comparing correlation between the light amount of the scattered light γ' and the hematocrit value and correlation between the light amount of the plasmon scattered light γ and the hematocrit value was performed.

In the reference experiment 1, in a state in which the measuring liquid, the plasma, the blood with the hematocrit value of 20%, or the blood with the hematocrit value of 40% was present in the flow path 41, the emission light α was applied to the metal film 30 while scanning the incident angle of the emission light α with respect to the metal film 30 and the light emitted above the measurement chip 10 was detected by the light receiving sensor 126 to measure the light amount of the light. At the same time, the reflected light of the emission light a was detected by a light receiving sensor (not illustrated), and the reflectance of the emission light α was determined.

Figure 4A:
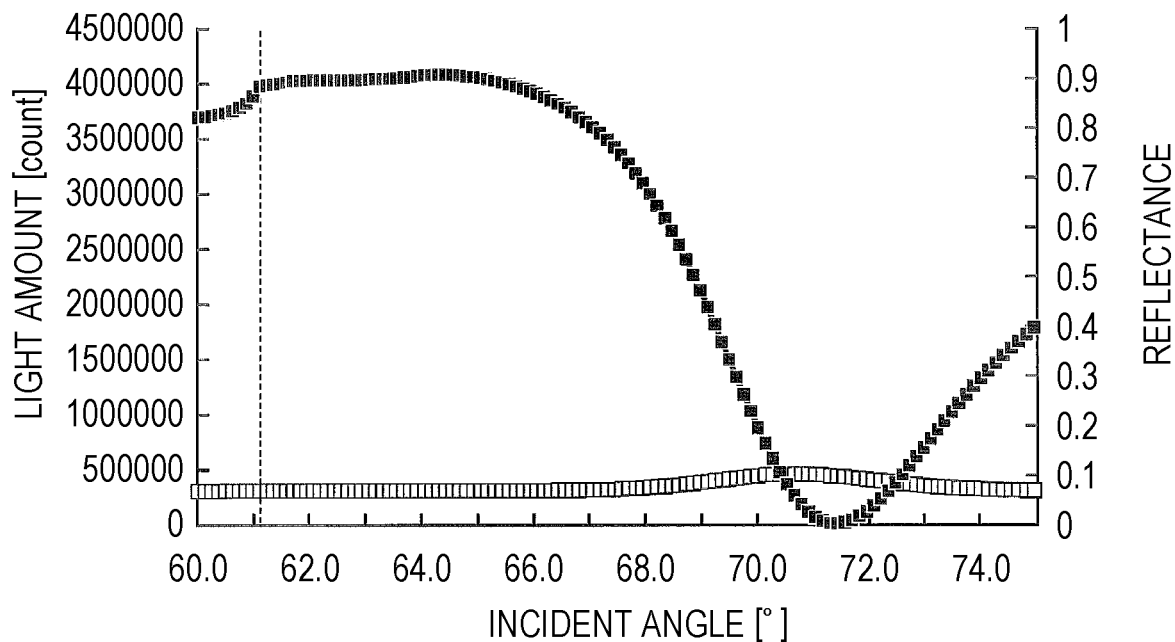
FIGS. 4A and 4B are graphs illustrating results of a reference experiment 1.
Figure 4B:
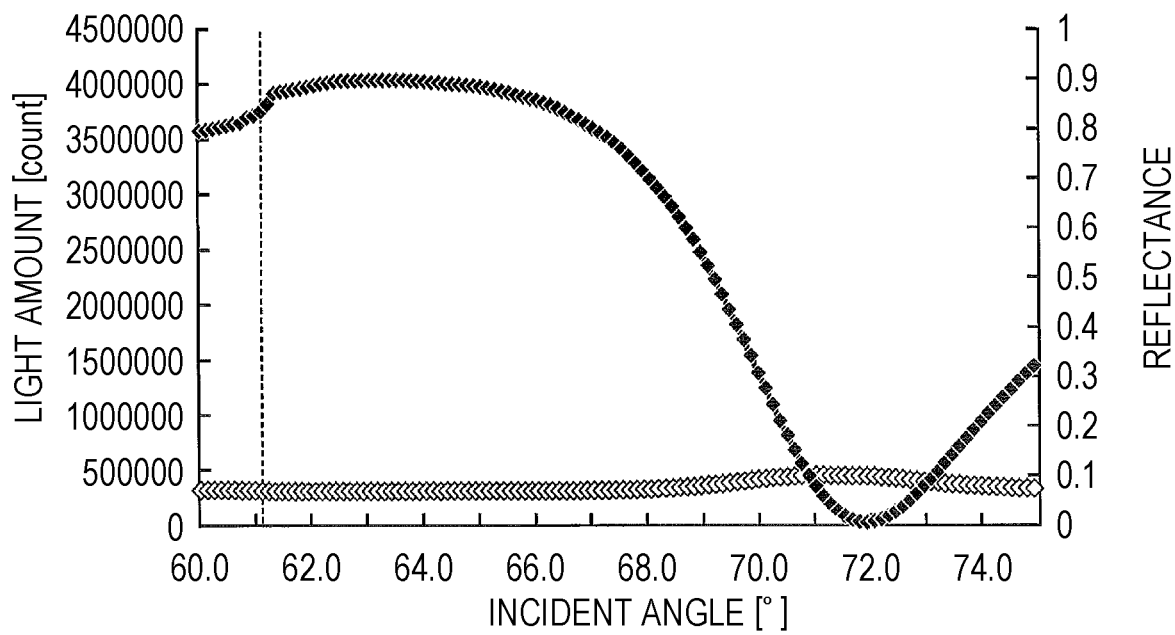
Figure 5A:
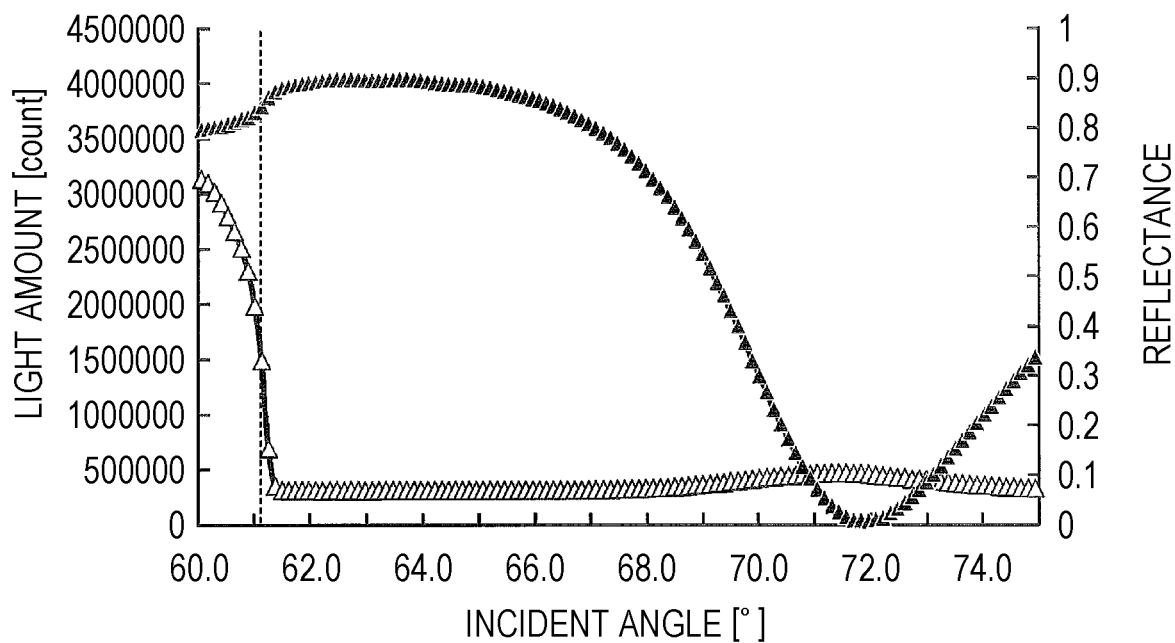
FIGS. 5A and 5B are graphs illustrating results of the reference experiment 1.
Figure 5B:
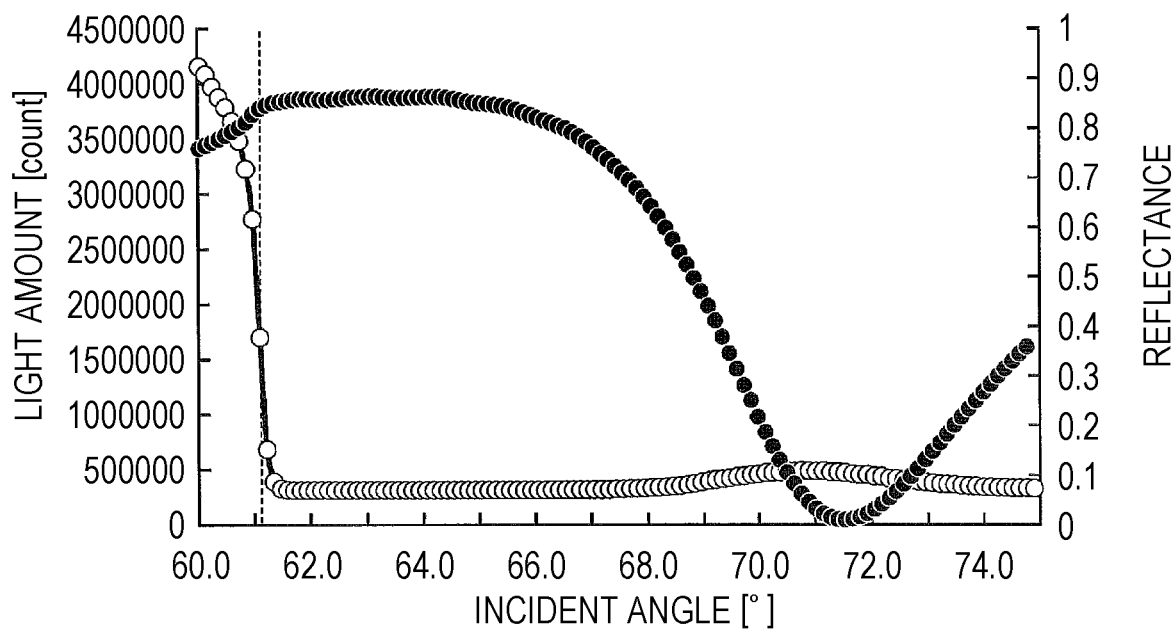

FIGS. 4A and 4B and FIGS. 5A and 5B are graphs illustrating results of the reference experiment 1, the graphs illustrating the relationship among the incident angle of the emission light α with respect to the metal film 30, the light amount of the scattered light γ' and the light amount of the plasmon scattered light γ, and the reflectance of the emission light α. In FIGS. 4A and 4B and FIGS. 5A and 5B, the light amount in an angular range (left side of a broken line in FIGS. 4A and 4B and FIGS. 5A and 5B) where the incident angle is smaller than the critical angle means the light amount of the scattered light γ', and the light amount in an angular range (right side of a broken line in FIGS. 4A and 4B and FIGS. 5A and 5B) where the incident angle is not smaller than the critical angle means the light amount of the plasmon scattered light γ. FIG. 4A is a measurement result in a state in which the measuring liquid is present in the flow path 41, FIG. 4B is a measurement result in a state in which the plasma is present in the flow path 41, FIG. 5A is a measurement result in a state in which the blood with the hematocrit value of 20% is present in the flow path 41, and FIG. 5B is a measurement result in a state in which the blood with the hematocrit value of 40% is present in the flow path 41. Also, in FIGS. 4A and 4B and FIGS. 5A and 5B, the incident angle (°) of the emission light α with respect to the metal film 30 is plotted along the horizontal axis, the light amount of the scattered light γ' or the plasmon scattered light γ (count) is plotted along the left vertical axis, and the reflectance of the emission light α is plotted along the right vertical axis. Furthermore, in FIGS. 4A and 5B and FIGS. 5A and 5B, the light amounts of the scattered light γ' and the plasmon scattered light γ are indicated by white symbols (□, ◇, △, and ○), the reflectance of the emission light α is indicated by black symbols (■, ♦, ▲, and ●).

In the graph illustrating the reflectance of the emission light α, a downward convex peak having a minimum value in the vicinity of 72 degrees is observed in a region in which the incident angle is 61 degrees or larger. This indicates that the surface plasmon resonance occurs in the metal film 30 in the region in which the incident angle is 61 degrees or larger. Regardless of whether blood cells are present in the specimen, the light amount of the plasmon scattered light γ hardly changes in the region in which the incident angle is 61 degrees or larger (refer to FIGS. 4A and 4B and FIGS. 5A and 5B).

On the other hand, as is apparent from the graph of the reflectance of the emission light α, the reflectance starts decreasing as the incident angle of the emission light α decreases with the vicinity of 61 degrees as a boundary. This indicates that the vicinity of 61 degrees is the critical angle. In a case where the specimen is the measuring liquid or plasma and the blood cells are not present in the specimen, in a region in which the incident angle is smaller than 61 degrees, the light amount of the scattered light γ' scarcely changes (refer to FIGS. 4A and 4B). In contrast, in a case where the specimen is the blood and the blood cells are present in the specimen, the light amount of scattered light γ' increases in the region in which the incident angle is smaller than 61 degrees (refer to FIGS. 5A and 5B). These results indicate that the emission light α is scattered by the blood cell component in the specimen as this passes through the specimen. As is clear from FIGS. 5A and 5B, it is understood that the intensity of the scattered light γ' caused by the blood cell component in the specimen is higher than the intensity of the plasmon scattered light γ.

Figure 6:
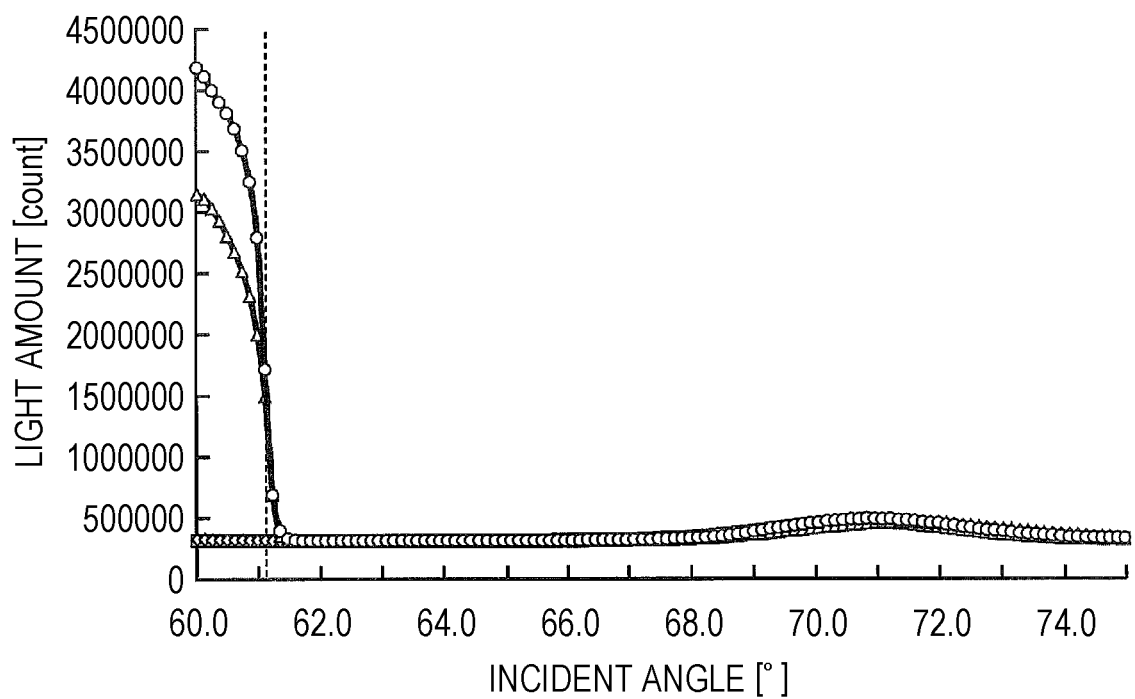
FIG. 6 is a graph illustrating correlation between a light amount of scattered light and a hematocrit value.

Next, the correlation between the light amount of the scattered light γ' and the hematocrit value is compared with the correlation between the light amount of the plasmon scattered light γ and the hematocrit value. FIG. 6 is a graph illustrating the correlation between the light amount of the scattered light γ' or the plasmon scattered light γ and the hematocrit value. FIG. 6 is a graph obtained by combing the graphs illustrating the relationship between the incident angle of the emission light α with respect to the metal film 30 and the light amount of the scattered light γ' or the plasmon scattered light γ in FIGS. 4A and 4B and FIGS. 5A and 5B. □ indicates the measurement result in the state in which the measuring liquid is present in the flow path 41 (FIG. 4A), ◇ indicates the measurement result in the state in which the plasma is present in the flow path 41 (FIG. 4B), Δ indicates the measurement result in the state in which the blood with the hematocrit value of 20% is present in the flow path 41 (FIG. 5A), and ○ indicates the measurement result in the state in which the blood with the hematocrit value of 40% is present in the flow path 41 (FIG. 5B). As illustrated in FIG. 6, the larger the hematocrit value in the specimen, the larger the light amount of scattered light γ' in the region in which the incident angle is smaller than 61 degrees. On the other hand, even if the hematocrit value in the specimen becomes large, the light amount of the plasmon scattered light γ in the region in which the incident angle is 61 degrees or larger hardly changes. That is, as is clear from FIG. 6, it is understood that the correlation between the light amount of the scattered light γ' and the hematocrit value is stronger than the correlation between the light amount of the plasmon scattered light γ and the hematocrit value.

From the results of the reference experiment 1, it is understood that the intensity of the scattered light γ' is higher than the intensity of the plasmon scattered light γ, and that the correlation between the light amount of the scattered light γ' and the hematocrit value is stronger than the correlation between the light amount of the plasmon scattered light γ and the hematocrit value. Therefore, it is understood that the hematocrit value may be determined with a higher degree of accuracy by detecting the scattered light γ' instead of the plasmon scattered light γ at the time of determining the hematocrit value.

(Reference Experiment 2)

An experiment was conducted to investigate a preferred range of the dilution ratio of the specimen when determining the hematocrit value. In the reference experiment 2, the whole blood of five types of hematocrit values (0%, 20%, 30%, 45%, and 65%) diluted such that the dilution ratio is one time (no dilution), three times, or 15 times was used as the specimen. In a state in which the measuring liquid is present in the flow path 41, the scattered light γ' emitted above the measurement chip 10 when applying the emission light α to the metal film 30 at the incident angle of 52 degrees was detected to measure the first optical blank value. Next, in a state in which the specimen is present in the flow path 41, the scattered light γ' emitted above the measurement chip 10 when applying the emission light α to the metal film 30 at the incident angle of 52 degrees was detected to measure the light amount of the scattered light γ'. By subtracting the first optical blank value from the light amount of the measured scattered light γ', the scattering component (signal component) due to the scattering in the specimen was calculated.

Figure 7:
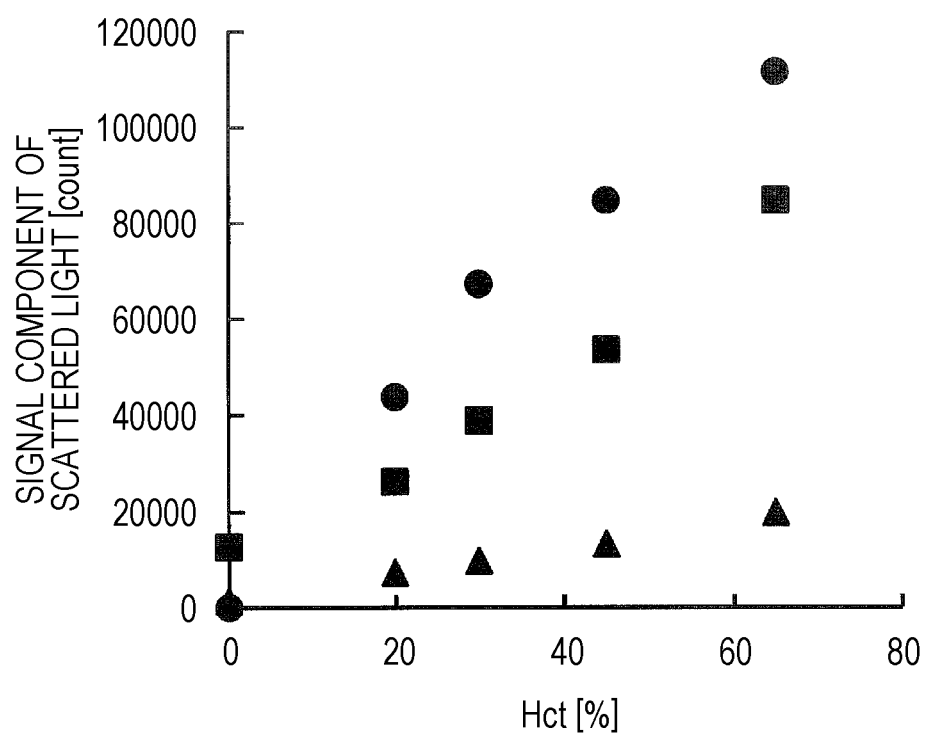
FIG. 7 is a graph illustrating results of a reference experiment 2.

FIG. 7 is a graph illustrating results of the reference experiment 2, the graph illustrating a relationship between the dilution ratio of the specimen and the correlation between the light amount of the scattered light γ' and the hematocrit value. In FIG. 7, a hematocrit value Hct (%) is plotted along the horizontal axis, and the signal component (count) of the scattered light γ' is plotted along the vertical axis. In addition, the results when the dilution ratio of the specimen is one time (no dilution) are indicated by black circles (●), the results when the dilution ratio of the specimen is three times are indicated by black squares (■), and the results when the dilution ratio of the specimen is 15 times are indicated by black triangles (▲).

As illustrated in FIG. 7, an inclination of the graph is larger as the dilution ratio of the specimen is smaller (the concentration of the specimen is higher). That is, it is understood that the correlation between the light amount of the scattered light γ' and the hematocrit value is stronger as the dilution ratio of the specimen is smaller (the concentration of the specimen is higher). Therefore, when detecting the scattered light γ for determining the hematocrit value, from a viewpoint of determining the hematocrit value with a high degree of accuracy, it is preferable that the concentration of the specimen is high. For example, the specimen is preferably the whole blood having the dilution ratio of one to 10 times, and is more preferably the whole blood having the dilution ratio of one to three times.

(Reference Experiment 3)

An experiment was conducted to investigate a preferable range of the thickness of the metal film 30. In this experiment, as for the metal films 30 having various thicknesses (10 to 80 nm), the reflected light of the emission light α emitted from the emission surface 23 of the measurement chip 10 when the emission light α having a wavelength of 660 nm is applied to the metal film 30 while changing the incident angle was detected by a light receiving sensor (not illustrated), and occurrence efficiency of the surface plasmon resonance was calculated on the basis of the light amount of the reflected light at a resonance angle at which the light amount of the reflected light of the emission light α becomes the minimum. As the metal film 30, a gold film was used.

Figure 8:
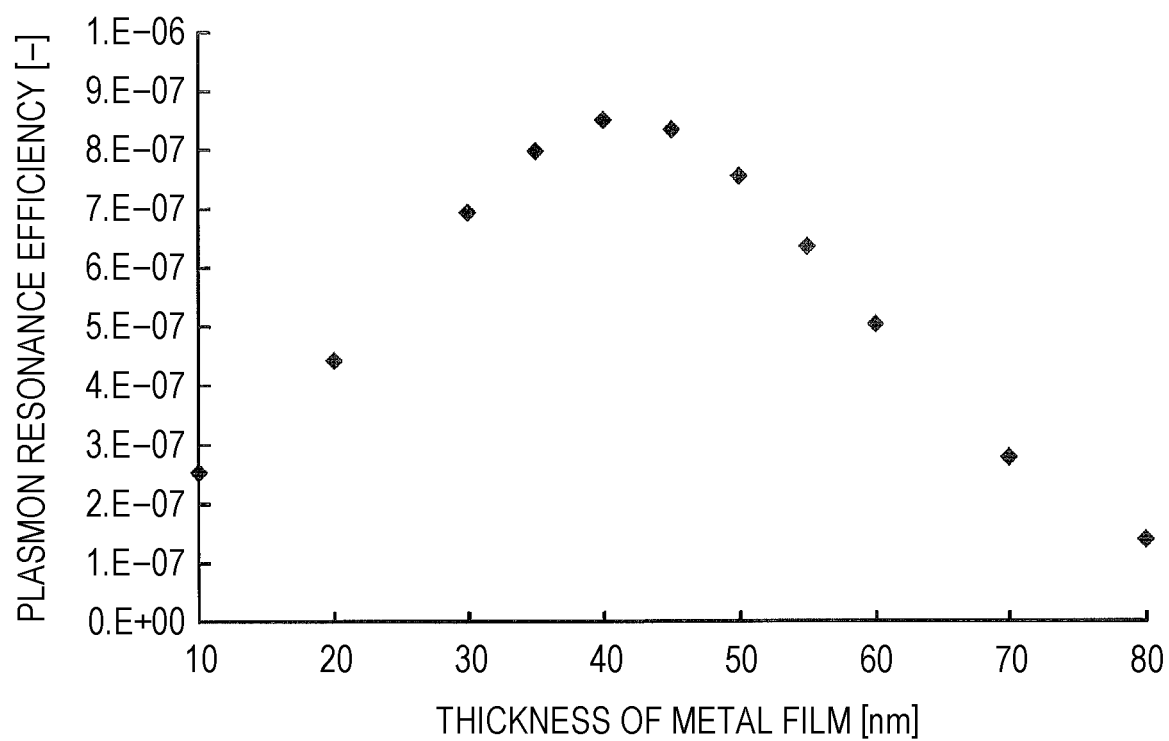
FIG. 8 is a graph illustrating results of a reference experiment 3.

FIG. 8 is a graph illustrating results of reference experiment 3. In FIG. 8, the thickness (nm) of the metal film 30 is plotted along the horizontal axis, and the occurrence efficiency of the surface plasmon resonance calculated on the basis of the light amount of the reflected light at the resonance angle is plotted along the vertical axis.

As illustrated in FIG. 8, the occurrence efficiency of the surface plasmon resonance is the largest when the thickness of the metal film 30 is in the vicinity of 40 nm. Therefore, it is understood that, in a case where the metal film 30 is the gold film, the signal indicating the amount of the substance to be measured may be detected with high intensity and the measurement value indicating the amount of the substance to be measured may be determined with a high degree of accuracy when the thickness of the metal film 30 is, for example, 30 to 55 nm.

Also, when the thickness of the metal film 30 is 30 to 55 nm, the transmittance of the emission light α to the metal film 30 is 5 to 30% (refer to FIG. 3B). That is, it is possible to detect the scattered light γ with high intensity by the high transmittance of the emission light α with respect to the metal film 30. From this point of view as well, the hematocrit value may be determined with a high degree of accuracy, and the amount of the substance to be measured in the specimen may be determined with a high degree of accuracy.

(SPFS Device)

Next, an example of the SPFS device for implementing the measurement method according to this embodiment is described. FIG. 2 is a configuration diagram illustrating an example of the configuration of the SPFS device 100. The SPFS device 100 includes the light emitting unit 110, a light detecting unit 120, a liquid sending unit 130, a transporting unit 140, and a control processing unit (processing unit) 150. The SPFS device 100 is used in a state in which the above-described measurement chip 10 is mounted on the chip holder (holder) 142 of the transporting unit 140.

The light emitting unit 110 emits the emission light α (first emission light $\alpha_1$ and second emission light $\alpha_2$). At steps S112 and S115 described above, the light emitting unit 110 emits the emission light α so as to be incident on the metal film 30 at the first incident angle. Also, at steps S113 and S117 described above, the light emitting unit 110 emits the emission light α so as to be incident on the metal film 30 at the second incident angle. That is, the first incident angle is the incident angle of the first emission light $\alpha_1$ applied to the metal film 30 in order to determine the hematocrit value. On the other hand, the second incident angle is the incident angle of the second emission light $\alpha_2$ applied to the metal film 30 in order to determine the measurement value indicating the amount of the substance to be measured. The first incident angle is smaller than the critical angle and the second incident angle is equal to or larger than the critical angle.

When detecting the scattered light γ', the light emitting unit 110 emits a P wave to the metal film 30 to the incident surface 21 at the first incident angle. The first emission light $\alpha_1$ at that time passes through the film depositing surface 22 to be emitted above the prism 20. Also, when detecting the fluorescence β or the plasmon scattered light γ, the light emitting unit 110 emits the P wave to the metal film 30 to the incident surface 21 at the second incident angle so that the surface plasmon resonance occurs on the metal film 30. The second emission light $\alpha_2$ at that time generates the localized field light for exciting the fluorescent substance on the surface of the metal film 30 when being applied to the metal film 30 via the prism 20 at an angle at which the surface plasmon resonance occurs.

The light emitting unit 110 includes a light source unit 111, the angle adjusting mechanism 112, and a light source control unit 113.

The light source unit 111 emits light collimated and having constant wavelength and light amount so that a shape of an irradiation spot on the rear surface of the metal film 30 is substantially circular. The light source unit 111 includes, for example, a light source, a beam shaping optical system, an APC mechanism, and a temperature adjusting mechanism (none of them is illustrated).

A type of the light source is not especially limited, and is, for example, the laser diode (LD). Other examples of the light source include laser light sources such as light emitting diodes and mercury lamps. The wavelength of the emission light α emitted from the light source is, for example, in a range of 400 nm to 1000 nm. In a case where the emission light α emitted from the light source is not a beam, the emission light α is converted into the beam by a lens, a mirror, a slit and the like. Also, in a case where the emission light α emitted from the light source is not monochromatic light, the emission light α is converted into the monochromatic light by a diffraction grating and the like. Furthermore, in a case where the emission light α emitted from the light source is not linear polarized light, the emission light α is converted into the linear polarized light by a polarizer and the like.

The beam shaping optical system includes, for example, a collimator, a band pass filter, a linear polarization filter, a half wavelength plate, a slit, a zoom means and the like. The beam shaping optical system may include all of them or a part of them.

The collimator collimates the emission light α emitted from the light source.

The band pass filter converts the emission light α emitted from the light source into narrow band light having only a central wavelength. This is because the emission light α emitted from the light source has a slight wavelength distribution width.

The linear polarization filter makes the emission light α emitted from the light source the linear polarized light.

The half wavelength plate adjusts a polarization direction of the light so that the P wave component is incident on the metal film 30.

The slit and the zoom means adjust a beam diameter, a contour shape and the like of the emission light α emitted from the light source so that the shape of the irradiation spot on the rear surface of the metal film 30 becomes a circle of a predetermined size.

The APC mechanism controls the light source so that an output of the light source is constant. More specifically, the APC mechanism detects a light amount of light branched from the emission light α with a photodiode not illustrated and the like. Then, the APC mechanism controls input energy by a recurrent circuit, thereby controlling the output of the light source constant.

The temperature adjusting mechanism is, for example, a heater, a Peltier element and the like. The wavelength and energy of the emission light α emitted from the light source might fluctuate depending on temperature. Therefore, by keeping the temperature of the light source constant by the temperature adjusting mechanism, the wavelength and energy of the emission light α emitted from the light source are controlled constant.

The angle adjusting mechanism 112 adjusts the incident angle of the emission light α with respect to the metal film 30 (interface (film depositing surface 22) between the prism 20 and the metal film 30). In order to apply the emission light α at the first or second incident angle to a predetermined position of the metal film 30 via the prism 20, the angle adjusting mechanism 112 relatively rotates an optical axis of the emission light α emitted from the light source and the chip holder 142. For example, the angle adjusting mechanism 112 rotates the light source unit 111 around an axis (axis perpendicular to a paper surface of FIG. 2) orthogonal to the optical axis of the emission light α on the metal film 30. At that time, a position of a rotational axis is set such that a position of the irradiation spot on the metal film 30 scarcely changes even if the incident angle is scanned. Especially, displacement of the irradiation position may be minimized by setting a position of a rotational center in the vicinity of an intersection (between the irradiation position on the film depositing surface 22 and the incident surface 21) of two optical axes of the emission light α emitted from the light source at both ends of the scanning range of the incident angle.

The light source control unit 113 controls various devices included in the light source unit 111 to control the emission of the emission light α from the light source unit 111. The light source control unit 113 is formed of, for example, a well-known computer or microcomputer including an arithmetic device, a control device, a storage device, an input device, and an output device.

The light detecting unit 120 detects light (for example, fluorescence β, scattered light γ', or plasmon scattered light γ) emitted from the measurement chip 10 on the metal film 30 when the light emitting unit 110 irradiates the metal film 30 via the prism 20. In this embodiment, the light detecting unit 120 outputs the signal indicating the light amount of the fluorescence β, the light amount of the scattered light γ', and the light amount of the plasmon scattered light γ which are detected to the control processing unit 150. The light detecting unit 120 includes a light receiving optical system unit 121, a position switching mechanism 122, and a sensor control unit 127.

The light receiving optical system unit 121 is arranged on a normal to the metal film 30 of the measurement chip 10. The light receiving optical system unit 121 includes a first lens 123, the optical filter 124, a second lens 125, and the light receiving sensor 126. The light receiving optical system unit 121 is arranged such that an optical axis thereof does not to coincide with the optical axis of the emission light α from the light emitting unit 110. As a result, it is possible to prevent the emission light α from directly entering the light receiving sensor 126 when detecting the fluorescence β, the scattered light γ', or the plasmon scattered light γ. As a result, it is possible to detect the fluorescence β, the scattered light γ', or the plasmon scattered light γ with a high S/N ratio.

The position switching mechanism 122 switches a position of the optical filter 124 such that the optical filter 124 is located on the optical path in the light receiving optical system unit 121 or the optical filter 124 is located out of the optical path partially or entirely. Specifically, when the light receiving sensor 126 detects the fluorescence β, the optical filter 124 is arranged on the optical path of the light receiving optical system unit 121, and when the light receiving sensor 126 detects the scattered light γ' and the plasmon scattered light γ, the optical filter 124 is arranged outside the optical path of the light receiving optical system unit 121 partially or entirely.

The first lens 123 is, for example, a condensing lens, and condenses light (signal) emitted from the upper side of the metal film 30. The second lens 125 is, for example, an image forming lens, and forms an image of the light condensed by the first lens 123 on a light receiving surface of the light receiving sensor 126. Between the two lenses, the light is a substantially parallel light flux.

The optical filter 124 is arranged between the first lens 123 and the second lens 125. When detecting fluorescence, the optical filter 124 transmits only the fluorescent component out of the light incident on the optical filter 124 and removes an excitation light component (plasmon scattered light γ). As a result, it is possible to guide only the fluorescent component to the light receiving sensor 126 and detect the fluorescence β with a high S/N ratio. Examples of types of the optical filter 124 include an excitation light reflecting filter, a short wavelength cutting filter, and a band pass filter. Examples of the optical filter 124 include a filter including a multilayer film which reflects a predetermined light component and a color glass filter which absorbs a predetermined light component.

The light receiving sensor 126 detects the fluorescence β, the scattered light γ', and the plasmon scattered light γ. By receiving the fluorescence β, the scattered light γ', and the plasmon scattered light γ by the same light receiving sensor 126, it is possible to prevent the SPFS device 100 from becoming larger and realize a low cost. The light receiving sensor 126 is arranged in a position different from a position overlapping with the optical axis of the emission light α. By detecting the scattered light γ' in a position different from the position overlapping with the optical axis of the emission light α, it is possible to detect the scattered light γ' with a high S/N ratio without detecting the emission light α emitted above the measurement chip 10 without being scattered in the specimen. The light receiving sensor 126 has high sensitivity capable of detecting weak fluorescence β from a minute amount of substance to be measured. The light receiving sensor 126 is, for example, a photomultiplier tube (PMT), an avalanche photodiode (APD), a silicon photodiode (SiPD) and the like.

The sensor control unit 127 controls detection of an output value of the light receiving sensor 126, management of sensitivity of the light receiving sensor 126 by the output value, change in the sensitivity of the light receiving sensor 126 for obtaining an appropriate output value and the like. The sensor control unit 127 is formed of, for example, a well-known computer or microcomputer including an arithmetic device, a control device, a storage device, an input device, and an output device.

The liquid sending unit 130 supplies the liquid in the liquid chip 50 into the flow path 41 of the measurement chip 10 held by the chip holder 142. Also, the liquid sending unit 130 removes the liquid from the flow path 41 of the measurement chip 10. The liquid sending unit 130 includes the pipette 131 and a pipette control unit 135.

The pipette 131 includes a syringe pump 132, a nozzle unit 133 connected to the syringe pump 132, and a pipette chip 134 attached to a tip end of the nozzle unit 133. Reciprocating motion of a plunger in the syringe pump 132 quantitatively sucks and discharges the liquid in the pipette chip 134.

The pipette control unit 135 includes a driving device of the syringe pump 132 and a moving device of the nozzle unit 133. The driving device of the syringe pump 132 is a device for reciprocating the plunger of the syringe pump 132 and includes, for example, a stepping motor. The moving device of the nozzle unit 133 freely moves, for example, the nozzle unit 133 in a vertical direction. The moving device of the nozzle unit 133 is formed of, for example, a robot arm, a two-axis stage, or a vertically movable turntable.

The pipette control unit 135 drives the syringe pump 132 to suck various types of liquid from the liquid chip 50 into the pipette chip 134. Then, the pipette control unit 135 moves the nozzle unit 133 to insert the pipette chip 134 into the flow path 41 of the measurement chip 10, and drives the syringe pump 132 to inject the liquid in the pipette chip 134 into the flow path 41. Also, after introducing the liquid, the pipette control unit 135 drives the syringe pump 132 to suck the liquid in the flow path 41 into the pipette chip 134. By sequentially exchanging the liquid in the flow path 41 in this manner, the capturing body and the substance to be measured are allowed to react in the reaction field (primary reaction) and the substance to be measured and the capturing body labeled with the fluorescent substance are allowed to react (secondary reaction). Also, the liquid sending unit 130 sucks or discharges the liquid in the liquid chip 50 in the above-described manner, thereby dispensing or diluting the specimen.

The transporting unit 140 transports the measurement chip 10 to fix. The transporting unit 140 includes a transporting stage 141 and the chip holder 142.

The transporting stage 141 moves the chip holder 142 in one direction and in the opposite direction. The transporting stage 141 also has a shape which does not interfere with the optical path of the light such as the emission light α, the reflected light of the emission light α, the fluorescence β, the scattered light γ', and the plasmon scattered light γ. The transporting stage 141 is driven by, for example, a stepping motor and the like.

The chip holder 142 is fixed to the transporting stage 141 and detachably holds the measurement chip 10. The chip holder 142 has a shape capable of holding the measurement chip 10 which does not interfere with the optical path of the light such as the emission light α, the reflected light of the emission light α, the fluorescence β, the scattered light γ', and the plasmon scattered light γ. For example, the chip holder 142 is provided with an opening through which the above-described light passes.

A temperature adjusting mechanism (not illustrated) such as a heater or a Peltier element is connected to the chip holder 142. Reaction efficiency of the reaction in the flow path 41 such as the primary reaction and the secondary reaction might vary depending on the temperature. Therefore, it is preferable to control the reaction efficiency constant and improve the measurement accuracy of the substance to be measured by keeping the temperature in the flow path 41 constant by the temperature adjusting mechanism via the chip holder 142.

The control processing unit 150 controls the angle adjusting mechanism 112, the light source control unit 113, the position switching mechanism 122, the sensor control unit 127, the pipette control unit 135, and the transporting stage 141. The control processing unit 150 also serves as a processing unit which processes a detection result of the light detecting unit 120 (light receiving sensor 126). In this embodiment, the control processing unit 150 determines the hematocrit value of the specimen on the basis of the detection result of the scattered light γ', and determines the measurement value indicating the amount of the substance to be measured in the specimen on the basis of the detection result of the fluorescence β. Along with this, the control processing unit 150 corrects the measurement value on the basis of the hematocrit value and determines the amount (concentration) of the substance to be measured in plasma or serum. In addition, specific information (for example, data regarding various conversion coefficients, dilution ratio, and calibration curve) used in the above-described process may be recorded in advance in the control processing unit 150. In this embodiment, a conversion coefficient for correcting (converting) the measurement value using the hematocrit value is recorded in advance in the control processing unit 150. The control processing unit 150 is formed of, for example, a well-known computer or a microcomputer including an arithmetic device, a control device, a storage device, an input device, and an output device.

(Optical Path in SPFS Device)

As illustrated in FIG. 2, the emission light α enters the prism 20 from the incident surface 21. When the emission light α entering the prism 20 is incident on the metal film 30 at the first incident angle, the scattered light γ' obtained when the emission light α (first emission light $\alpha_1$) is scattered by the specimen when passing through the metal film 30, the liquid in the flow path 41, and the flow path lid 40 is emitted above the measurement chip 10. Finally, the scattered light γ' reaches the light receiving sensor 126. Note that although not especially illustrated, a part of the emission light α (first emission light $\alpha_1$) is reflected by the metal film 30 to become the reflected light, and the reflected light is emitted out of the prism 20 from the emission surface 23.

On the other hand, when the emission light α entering the prism 20 is incident on the metal film 30 at the second incident angle being a total reflection angle at which the SPR occurs, the localized field light is generated on the metal film 30. By this localized field light, the fluorescent substance which labels the substance to be measured present on the metal film 30 is excited and the fluorescence β is emitted. The SPFS device 100 detects the fluorescence β emitted from the fluorescent substance. Note that, although not especially illustrated, the reflected light of the emission light α (second emission light $\alpha_2$) at the metal film 30 is emitted out of the prism 20 from the emission surface 23.

(Effect)

In the measurement method according to this embodiment, in order to determine the hematocrit value of the specimen, the scattered light γ' obtained when the first emission light $\alpha_1$ is scattered in the specimen when the first emission light $\alpha_1$ is applied to the metal film 30 at the first incident angle smaller than the critical angle is detected. The scattered light γ' has higher intensity and higher correlation with the hematocrit value than the plasmon scattered light γ. Therefore, in the measurement method according to this embodiment, it is possible to determine the hematocrit value with a higher degree of accuracy than in a case of detecting the plasmon scattered light γ to determine the hematocrit value of the specimen. Therefore, with the measurement method according to this embodiment, it is possible to determine the hematocrit value of the specimen with a high degree of accuracy and to determine the amount (concentration) of the substance to be measured in the plasma with a high degree of accuracy. Also, in the measurement method according to this embodiment, it is possible to measure the hematocrit value with a high degree of accuracy without newly adding a device for measuring the hematocrit value, so that a manufacturing cost and a measuring cost of the measurement device are not increased.

[Variation]

The measurement method according to the present invention is not limited to the measurement method according to the above-described embodiment, and the order of each step may be exchanged as necessary. FIG. 9 is a flowchart illustrating an example of a measurement method according to a variation. For example, as illustrated in FIG. 9, after a step of detecting a fluorescence signal (step S117), a step of measuring a first optical blank value (step S112) and a step of detecting scattered light γ' (step S115) may be performed.

A method of performing steps S112 and S115 described above for determining a hematocrit value after detecting fluorescence β is particularly effective means in a case of using whole blood having a high dilution ratio, for example, whole blood having a dilution ratio of 10 times or more as a specimen.

In the above-described embodiment, the specimen used at the step of performing the primary reaction is the same as the specimen used at the step of detecting the scattered light γ'. Therefore, in a case of using the specimen having the large dilution ratio in the primary reaction, detection accuracy of the scattered light γ' is deteriorated. On the other hand, in the measurement method according to the variation, even in a case where the whole blood having the dilution ratio of 10 times or larger is used as the specimen in the primary reaction (step S114), it is possible to separately prepare the specimen having a lower dilution ratio (higher concentration) than the specimen to use at the step of detecting the scattered light γ' (step S115). As a result, it is possible to obtain a measurement value indicating an amount of a substance to be measured with a high degree of accuracy by using the specimen having the large dilution ratio (low concentration), and to obtain the hematocrit value with a high degree of accuracy by using the specimen having the small dilution ratio (high concentration). As a result, it is possible to determine the amount (concentration) of the substance to be measured in plasma with a higher degree of accuracy.

In the measurement method according to the above-described embodiment, as compared with the measurement method according to the above-described variation, the hematocrit value may be measured using the specimen provided in the flow path 41 at the step of performing the primary reaction, so that it is possible to further shorten the measurement time of the substance to be measured. Also, in the measurement method according to the above-described embodiment, since the step of the secondary reaction (step S116) and the step of detecting the fluorescence signal (step S117) are performed after the step of measuring the first optical blank value (step S112), the fluorescence signal does not mix into the first optical blank value and the hematocrit value may be measured with a higher degree of accuracy.

Note that a mode of performing the step of determining the enhancement angle (step S111), the step of measuring the first optical blank value (step S112), the step of measuring the second optical blank value (step S113), and the step of performing the primary reaction (step S114) in this order is described in this embodiment. However, in the measurement method according to the present invention, the order is not limited thereto. For example, the enhancement angle may be determined after the primary reaction is performed, or the first optical blank value and the second optical blank value may be measured after the primary reaction is performed.

Also, the step of determining the enhancement angle (step S111) may be performed after the step of measuring the first optical blank value (step S112) is performed. However, from a viewpoint of reducing the number of times of switching the position of the optical filter 124 and shortening the measurement time of the substance to be measured, it is preferable to perform the step of measuring the second optical blank value (step S113) after performing the step of determining the enhancement angle (step S111) and the step of measuring the first optical blank value (step S112).

In the above-described variation, the step of performing the secondary reaction (step S116) is performed after the step of performing the primary reaction (step S114) (two-step method). However, the timing of labeling the substance to be measured with the fluorescent substance is not especially limited. For example, it is possible to add the labeling solution to the specimen to label the substance to be measured in advance with the fluorescent substance before the specimen is introduced into the flow path 41 of the measurement chip 10. It is also possible to inject the specimen and the labeling solution simultaneously into the flow path 41 of the measurement chip 10. In the former case, the specimen is injected into the flow path 41 of the measurement chip 10, so that the substance to be measured labeled with the fluorescent substance is captured by the capturing body. In the latter case, the substance to be measured is labeled with the fluorescent substance and the substance to be measured is captured by the capturing body. In either case, both the primary reaction and the secondary reaction may be completed by introducing the specimen into the flow path 41 of the measurement chip 10 (one-step method).

Note that, although the mode of detecting the fluorescence β from the fluorescent substance as the signal by utilizing the SPFS method is described in the above-described embodiment, the present invention is not limited to this mode. For example, it is also possible to detect the reflected light of the emission light α as the measurement value by using an SPR method.

Also, although the measurement method including the step of determining the enhancement angle (step S111) is described in the above-described embodiment, it is not necessary that the measurement method according to the present invention include the step of determining the enhancement angle. In this case, the enhancement angle may be calculated in advance on the basis of factors such as a design of the measurement chip 10 and the refractive index of the liquid provided in the flow path 41.

Furthermore, in the above-described embodiment, the mode of applying the first emission light $\alpha_1$ (first light) when detecting the scattered light γ' and the second emission light $\alpha_2$ (second light) when detecting the fluorescence β from the same light source to the metal film 30 is described. However, the measurement method according to the present invention is not limited to this mode, and it is possible to apply the first emission light $\alpha_1$ (first light) when detecting the scattered light γ' and the second emission light $\alpha_2$ (second light) when detecting the fluorescence β from different light sources to the metal film 30. From a viewpoint of preventing an increase in size of the SPFS device 100 and realizing cost reduction, it is more preferable to use the same light source.

This application claims priority based on Japanese Patent Application No. 2016-179396 filed on Sep. 14, 2016. The contents described in the application specification and illustrated in drawings are herein entirely incorporated.

INDUSTRIAL APPLICABILITY

Since the measurement method of the substance to be measured according to the present invention may detect the substance to be measured with high reliability, this is useful for examining diseases, for example.

REFERENCE SIGNS LIST

10 Measurement chip
20 Prism
21 Incident surface

22 Film depositing surface
23 Emission surface
30 Metal film
40 Flow path lid
41 Flow path
50 Liquid chip
100 SPFS device
110 Light emitting unit
111 Light source unit
112 Angle adjusting mechanism
113 Light source control unit
120 Light detecting unit
121 Light receiving optical system unit
122 Position switching mechanism
123 First lens
124 Optical filter
125 Second lens
126 Light receiving sensor
127 Sensor control unit
130 Liquid sending unit
131 Pipette
132 Syringe pump
133 Nozzle unit
134 Pipette chip
135 Pipette control unit
140 Transporting unit
141 Transporting stage
142 Chip holder
150 Control processing unit (processing unit)
α Emission light
$α_1$ First emission light
$α_2$ Second emission light
β Fluorescence
γ Plasmon scattered light
γ' Scattered light

The invention claimed is:

1. A measurement method for measuring an amount of a substance to be measured in a specimen including whole blood using surface plasmon resonance, the measurement method comprising:
    preparing a measurement chip including a prism including an incident surface and a film depositing surface, a metal film arranged on the film depositing surface, and a capturing body immobilized on the metal film;
    detecting scattered light obtained when first light passing through the metal film and the specimen is scattered in the specimen when the first light is applied to the metal film at a first incident angle smaller than a critical angle from a prism side in a state in which the specimen is present on the metal film;
    detecting a signal indicating the amount of the substance to be measured generated in the measurement chip when second light is applied to the metal film at a second incident angle equal to or larger than the critical angle from the prism side in a state in which the substance to be measured is captured by the capturing body and the specimen is not present on the metal film; and
    correcting a measurement value indicating the amount of the substance to be measured determined from the detected signal on the basis of a hematocrit value of the specimen determined from a light amount of the detected scattered light.

2. The measurement method according to claim 1, wherein the first incident angle is equal to or smaller than an angle smaller than the critical angle by five degrees.

3. The measurement method according to claim 2, wherein the first incident angle is equal to or larger than an angle smaller than the critical angle by 10 degrees.

4. The measurement method according to claim 2, further comprising
    detecting plasmon scattered light generated in the measurement chip when light is applied from the prism side while scanning an incident angle and determining an enhancement angle being the incident angle when a light amount of the plasmon scattered light becomes maximum,
    wherein, at the detecting the signal, the second light is applied to the metal film at the enhancement angle.

5. The measurement method according to claim 2, wherein light transmittance of the metal film when P-polarized light is applied to the metal film at the incident angle of 50 degrees is 3 to 30%.

6. The measurement method according to claim 2, wherein the specimen is the whole blood having a dilution ratio of one to 10 times.

7. The measurement method according to claim 2, wherein the first light is P-polarized light having a wavelength of 600 to 700 nm.

8. The measurement method according to claim 2, wherein the first light and the second light are applied from the same light source to the metal film.

9. The measurement method according to claim 2, wherein at the detecting the scattered light, the scattered light is detected at a position different from a position overlapping with an optical axis of the first light.

10. The measurement method according to claim 1, further comprising
    detecting plasmon scattered light generated in the measurement chip when light is applied from the prism side while scanning an incident angle and determining an enhancement angle being the incident angle when a light amount of the plasmon scattered light becomes maximum,
    wherein, at the detecting the signal, the second light is applied to the metal film at the enhancement angle.

11. The measurement method according to claim 10, wherein the scattered light and the plasmon scattered light are detected by the same light receiving sensor.

12. The measurement method according to claim 1, wherein light transmittance of the metal film when P-polarized light is applied to the metal film at the incident angle of 50 degrees is 3 to 30%.

13. The measurement method according to claim 12, wherein a thickness of the metal film is 30 to 60 nm.

14. The measurement method according to claim 1, wherein the specimen is the whole blood having a dilution ratio of one to 10 times.

15. The measurement method according to claim 14, wherein the specimen is the whole blood having the dilution ratio of one to three times.

16. The measurement method according to claim 1, wherein the first light is P-polarized light having a wavelength of 600 to 700 nm.

17. The measurement method according to claim 1, wherein the first light and the second light are applied from the same light source to the metal film.

18. The measurement method according to claim 17, wherein the first incident angle and the second incident angle are switched by rotating the light source.

19. The measurement method according to claim 1, wherein at the detecting the scattered light, the scattered light is detected at a position different from a position overlapping with an optical axis of the first light.

20. The measurement method according to claim 1, wherein the signal is fluorescence emitted from a fluorescent substance which labels the substance to be measured.

* * * * *